US010285646B1

(12) United States Patent
Grant et al.

(10) Patent No.: US 10,285,646 B1
(45) Date of Patent: May 14, 2019

(54) CONNECTION QUALITY ASSESSMENT FOR EEG ELECTRODE ARRAYS

(71) Applicant: CeriBell, Inc., Mountain View, CA (US)

(72) Inventors: Alexander M. Grant, Redwood City, CA (US); Jianchun Yi, San Jose, CA (US); Bradley G. Bachelder, Menlo Park, CA (US); Raymond Woo, Los Altos, CA (US); Josef Parvizi, Palo Alto, CA (US); Xingjuan Chao, Palo Alto, CA (US)

(73) Assignee: CeriBell, Inc., Mountain View, CA (US)

( * ) Notice: Subject to any disclaimer, the term of this patent is extended or adjusted under 35 U.S.C. 154(b) by 0 days.

(21) Appl. No.: 15/906,375

(22) Filed: Feb. 27, 2018

(51) Int. Cl.
*A61B 5/04* (2006.01)
*A61B 5/0476* (2006.01)
(Continued)

(52) U.S. Cl.
CPC ........ *A61B 5/6843* (2013.01); *A61B 5/04001* (2013.01); *A61B 5/04012* (2013.01); *A61B 5/0422* (2013.01); *A61B 5/0478* (2013.01); *A61B 5/0492* (2013.01); *A61B 5/6803* (2013.01); *A61B 5/7221* (2013.01); *A61N 1/025* (2013.01); *A61N 1/0452* (2013.01); *A61N 1/0456* (2013.01); *A61N 1/0492* (2013.01); *A61N 1/0551* (2013.01); *A61N 1/36007* (2013.01); *A61N 1/37* (2013.01); *A61B 2562/0209* (2013.01); *A61B 2562/043* (2013.01)

(58) Field of Classification Search
CPC ............ A61N 1/36014; A61N 1/36521; A61B 5/0006; A61B 5/00476; A61B 5/0476; A61B 5/0478; A61B 5/0482; A61B 5/053; A61B 5/0531; A61B 5/04001; A61B 5/6803; A61B 5/7221
See application file for complete search history.

(56) References Cited

U.S. PATENT DOCUMENTS 5,713,935 A  2/1998 Prutchi et al.
7,865,236 B2  1/2011 Cory et al.
(Continued)

OTHER PUBLICATIONS

International search report with written opinion dated Apr. 30, 2018 for PCT/US2018/019902.

*Primary Examiner* — Allen Porter
(74) *Attorney, Agent, or Firm* — Wilson Sonsini Goodrich and Rosati, P.C.

(57) ABSTRACT

Systems, devices, and methods are provided to assess connection quality between the electrodes of a bioelectrical signal measurement and/or electrical stimulation device and the tissue, typically skin, of the subject. A test signal is provided to a first electrode, voltage differences between the first electrode and additional electrodes are determined, an impedance of the first electrode is determined based on the voltages differences, and the determined impedance indicates connection quality. This process is typically repeated for all of the electrodes to determine connection quality. The user or subject can be alerted if the connection quality is poor, and the bioelectrical signal that is recorded can be provided with data points indicating connection quality during the signal recording.

21 Claims, 14 Drawing Sheets

(51) Int. Cl.
*A61B 5/00* (2006.01)
*A61B 5/0478* (2006.01)
*A61B 5/0492* (2006.01)
*A61B 5/042* (2006.01)
*A61N 1/04* (2006.01)
*A61N 1/05* (2006.01)
*A61N 1/36* (2006.01)
*A61N 1/37* (2006.01)
*A61N 1/02* (2006.01)

(56) References Cited

U.S. PATENT DOCUMENTS

| | | |
|---|---|---|
| 9,820,670 B2 | 11/2017 | Parvizi et al. |
| 9,888,884 B2 | 2/2018 | Chafe et al. |
| 2002/0040192 A1 | 4/2002 | Prutchi |
| 2003/0233129 A1* | 12/2003 | Matos ................ A61B 5/0006 607/5 |
| 2008/0051845 A1* | 2/2008 | Mentelos ............ A61B 5/0424 607/28 |
| 2012/0143020 A1* | 6/2012 | Bordoley ............ A61B 5/1114 600/301 |
| 2013/0324878 A1 | 12/2013 | Chafe et al. |
| 2014/0051044 A1 | 2/2014 | Badower et al. |
| 2014/0247058 A1* | 9/2014 | Mortara ............. A61B 5/0424 324/601 |
| 2015/0359492 A1 | 12/2015 | Giovangrandi et al. |
| 2018/0049661 A1 | 2/2018 | Parvizi et al. |
| 2018/0345006 A1* | 12/2018 | Ambrose ........... A61N 1/36025 |

* cited by examiner

CONNECTION QUALITY ASSESSMENT FOR EEG ELECTRODE ARRAYS

CROSS-REFERENCE

N/A

BACKGROUND

The present disclosure relates generally to the field of measuring electrical signals from living subjects (e.g., electrical signals indicative of brain activity and/or heart activity) and providing electrical signals to living subjects (e.g., for neurostimulation or muscle stimulation). In particular, the present disclosure relates to systems, devices, and methods for calibrating the connection between the electrode(s) of such measurement and/or stimulation devices and the tissue of the living subject, typically skin.

The ability to measure signals from a living subject (e.g., those relating to the living subject's bodily functions) can be beneficial for many medical and diagnostic applications. Electrical signals from the brain (i.e., electroencephalography (EEG) signals) can be measured to ascertain brain activity related to abnormal brain function, to monitor spatial and/or temporal progression of brain disease, to aid surgical or nonsurgical intervention by localizing disease-sites in the brain, to monitor brain activity of a healthy subject or a subject of unknown health status when the subject experiences a variety of stimuli and lack of stimuli, etc. Electrical signals from the heart (i.e., electrocardiography (ECG or EKG) signals) can be measured to determine the rate and rhythm of heart beats, the size and position of the heart chambers, the presence of any damage to the cardiac and/or myocardial tissue, the effect of cardiac drugs, the function of cardiac pacing devices, etc. Electrical signals from skeletal muscles (i.e., electromyography (EMG) signals) can be measured to determine medical abnormalities with the skeletal muscles, their activation levels, their recruitment order, to analyze the biomechanics of movement, etc.

The ability to deliver electrical signals to a living subject can also be beneficial for many medical and therapeutic applications. Electrical signals may be delivered to the heart to pace the rate and rhythm of heart beats, and in some cases, for defibrillation of the heart. Electrical signals may be applied to various parts of the nervous system to upregulate and/or downregulate various nerve and nerve-related functions. For example, the spinal cord may be stimulated to treat pain, facilitate injury rehabilitation, restore cardiac function, and lower blood pressure, among other indications. The peripheral nerves may also be stimulated to treat pain, facilitate injury rehabilitation, treat incontinence, and lower blood pressure, among other indications. Electrical signals may be delivered to the skeletal muscles to diagnose responsiveness, facilitate injury rehabilitation, accelerate muscle recovery, improve metabolism, tone skeletal muscle tissue, and as an alternative to weight-bearing exercise, among other purposes. In some cases, the electrical signals delivered may be varied in accordance with other electrical signals measured to provide a form of feedback therapy.

The measurement of electrical signals from a living subject and the delivery of electrical signals are often performed through connection(s) between measurement and/or stimulation electrode(s) and tissue of a patient. In many cases, the connection will be between the skin and the electrode(s). For example, EEG headsets contact EEG electrodes with the scalp of the subject, ECG electrodes are typically contacted to skin on the chest of a subject, EMG electrodes are typically contacted to skin over the target skeletal muscles, and, in some cases, nerves and muscles may be stimulated externally from external electrode(s) contacting skin adjacent the target nerves and/or muscles. The connection between the electrode(s) and skin may not always be ideal for many reasons—such as skin moisture and quality not being ideal for electrode contact, the presence of hair, the presence of regions of thickened and/or hardened skin, the presence of dirt, undesired fluids, or other residue, to name a few examples. Hence, the electrode-to-skin connection may often need to be assessed so that, if appropriate, a medical professional may re-position the electrode, clean the skin and/or electrode, or otherwise re-adjust the connection as needed to have a more ideal electrode connection for the intended measurement and/or diagnosis. In other cases, the connection will be between the electrode(s) and other tissue. For example, the connection may be between dura mater in the epidural space and the electrode lead(s) for spinal cord simulators, between the pacing lead(s) and cardiac tissue for pacing devices, the electrode(s) and skeletal muscle tissue for skeletal muscle stimulators, etc. Connection quality between the electrode(s) and the tissue may again be important to obtain high quality measurements and/or provide the stimulation at the desired levels.

In many cases, the connection between measurement or stimulation electrode(s) and tissue of the subject is assessed before measurement and/or stimulation. Measurement and/or stimulation, in some cases, however, may be long-term and continuous. For example, measurements and/or stimulation may be undertaken for at least 30 minutes, at least an hour, at least a day, or at least a week or more in many applications. And, connection quality may deteriorate or at least vary over the long measurement and/or stimulation time period. Many currently used connection quality assessment methods, however, cannot determine connection quality while measurement and/or stimulation are occurring. For example, many connection quality assessment methods depend on the use of a further reference electrode and/or reference current, which in many cases cannot be present when measurement and/or stimulation are undertaken.

There are therefore needs for improving the way the connection quality between the electrodes of various measurement or stimulation devices is assessed. There are also needs for connection quality assessments methods that are usable concurrently with measurement and/or stimulation, so that electrode connections can be re-adjusted as necessary throughout the desired measurement and/or stimulation time period, the measurement and/or stimulation can be dynamically adjusted based on the current connection quality, the measurement and/or stimulation signal can be recorded along with connection quality assessment to provide signal recordings with more data points for later analysis, to name a few desirable purposes.

SUMMARY

The present disclosure relates generally to the field of measuring electrical signals detected from living subjects (e.g., electrical signals indicative of brain activity and/or heart activity) and providing electrical signals to living subjects (e.g., for neurostimulation or muscle stimulation). In particular, the present disclosure relates to systems, devices, and methods for calibrating the connection between electrode(s) of such measurement and/or stimulation devices and the tissue of the living subject, typically skin. An exemplary measurement and/or stimulation apparatus may comprise a plurality of electrodes configured to contact the skin of a subject to measure and/or convey one or more electrical signals. Voltage differentials between the different electrodes may be used, according to embodiments of the present disclosure, to determine impedances associated with the electrodes. The determined impedances can provide an indicator for connection quality, and, if connection quality is poor, the apparatus may notify the subject or other user and may record connection quality data points in parallel with measured electrical signals. Hence, the subject or other user may be prompted to improve connection quality and the reliability of the measured electrical signals, and medical professionals may take into account the record of connection quality while later analyzing the electrical signals that are measured and recorded.

Aspects of the present disclosure provide methods of assessing quality of a connection between an electrical sensor or stimulator and tissue of a subject. An electrical sensor or stimulator may be provided (step (a)). The electrical sensor or stimulator may comprise a plurality of electrodes, not including a common ground or reference electrode. The plurality of electrodes may be contacted to tissue of a subject (step (b)). A test signal may be provided to the tissue of the subject through a first electrode of the plurality of electrodes (step (c)). At least one voltage difference between the first electrode and a second electrode may be determined in response to the test signal (step (d)). An impedance of the first electrode may be determined in response to the at least one voltage difference (step (e)). One or more of the subject or a user may be notified that connection quality of the first electrode is poor if the determined impedance of the first electrode is above a first predetermined impedance threshold (step (f)).

The first and second electrodes may be adjacent one another.

The electrical sensor or stimulator may comprise one or more of a wearable headset, an electrode patch, or an electrode lead advanceable through the tissue, a body cavity, or a body lumen. The wearable sensor may comprise a wearable headset.

The plurality of electrodes may comprise a first set of electrodes on one side of the electrical sensor or stimulator and a second set of electrodes on a second side of the electrical sensor or stimulator opposite the first side. The electrical sensor or stimulator may comprise a wearable headset comprising a first hemisphere and a second hemisphere. The plurality of electrodes may comprise a first set of electrodes on the first hemisphere and a second set of electrodes on the second hemisphere.

The tissue of the subject may comprise a skin of the subject, muscle tissue of the subject, or neural tissue of the subject. The tissue of the subject comprises a skin of the subject. The skin of the subject may comprise a scalp of the subject.

The test signal may have a predetermined frequency, and the impedance may be determined in response to the predetermined frequency. The predetermined frequency may be in a range of 1 to 150 Hz. The test signal may be provided through the first electrode with a first predetermined current.

To determine the at least one voltage difference, a first voltage difference between the first electrode and the second electrode may be determined and a second voltage difference between the first electrode and a third electrode may be determined. To determine the impedance, a first impedance between the first electrode and the second electrode may be determined in response to the first voltage difference, a second impedance between the first electrode and the third electrode in response to the second voltage difference may be determined, a lesser of the first and second impedances may be determined, and the lesser of the first and second impedances may be assigned as the determined impedance of the first electrode.

The predetermined acceptable impedance threshold may be in a range of 0 to 100 k$\Omega$.

Steps (c) to (e) may be repeated for at least one additional electrode of the plurality of electrodes to determine a plurality of impedances for the plurality of electrodes.

The one or more of the subject or the user may be notified by providing one or more of an audio or visual signal or alarm.

An electrical stimulation signal may further be provided with the electrical sensor or stimulator. The electrical stimulation signal may provide stimulation of one or more of a nerve, a spinal cord nerve, a peripheral nerve, a skeletal muscle, a smooth muscle, or cardiac tissue.

A bioelectrical signal may be measured from the subject as the impedance of the first electrode is determined. The bioelectrical signal may comprise one or more of an EEG signal, an ENG signal, an ECG signal, an EKG signal, or an EMG signal. The bioelectrical signal may further be recorded to generate a signal recording, and the signal recoding pay be provided with connection quality data points in response to the determined impedance.

The plurality of electrodes may be coupled to a processor, and the processor may be configured to one or more of generate the test signal, determine the at least one voltage difference, or determine the impedance of the first electrode.

Aspects of the present disclosure provide apparatuses for one or more of measuring a bioelectrical signal from a subject or providing an electrical stimulation signal to the subject. An exemplary apparatus may comprise a plurality of electrodes configured to contact tissue of a subject and a processor coupled to the plurality of electrodes and configured to: (i) provide a test signal to the tissue of the subject through a first electrode of the plurality of electrodes, (ii) determine at least one voltage difference between the first electrode and a second electrode in response to the test signal, (iii) determine an impedance of the first electrode in response to the determined at least one voltage difference, and (iv) notify one or more of the subject or a user that connection quality of the first electrode is poor if the determined impedance of the first electrode is above a first predetermined impedance threshold.

The first and second electrodes may be adjacent one another.

The apparatus may further comprise one or more of a wearable headset coupled to the plurality of electrodes, an electrode patch coupled to one or more electrodes of the plurality of electrodes, or an electrode lead coupled to one or more electrodes of the plurality of electrodes and advanceable through the tissue, a body cavity, or a body lumen.

The apparatus may further comprise a wearable base coupled to the plurality of electrodes. The plurality of electrodes may comprise a first set of electrodes on one side of the wearable base and a second set of electrodes on a second side of the wearable base opposite the first side. The wearable base may comprise a wearable headset comprising a first hemisphere and a second hemisphere, and the plurality of electrodes may comprise a first set of electrodes on the first hemisphere and a second set of electrodes on the second hemisphere.

The test signal may have a predetermined frequency, and the impedance may be determined in response to the predetermined frequency. The predetermined frequency may be in a range of 1 to 150 Hz. The test signal may be provided through the first electrode with a first predetermined current.

To determine the at least one voltage difference, a first voltage difference between the first electrode and the second electrode may be determined and a second voltage difference between the first electrode and a third electrode may be determined. To determine the impedance, a first impedance between the first electrode and the second electrode may be determined in response to the first voltage difference, a second impedance between the first electrode and the third electrode in response to the second voltage difference may be determined, a lesser of the first and second impedances may be determined, and the lesser of the first and second impedances may be assigned as the determined impedance of the first electrode.

The predetermined acceptable impedance threshold may be in a range of 0 to 100 kΩ.

The processor may be configured to repeat steps (i) to (iii) for at least one additional electrode of the plurality of electrodes to determine a plurality of impedances for the plurality of electrodes.

The processor may be configured to generate a notification to the one or more of the subject or the user by providing one or more of an audio or visual signal or alarm.

The plurality of electrodes may be configured to measure a bioelectrical signal from the subject as the impedance of the first electrode is determined. The bioelectrical signal may comprise one or more of an EEG signal, an ENG signal, an ECG signal, an EKG signal, or an EMG signal.

The processor may be configured to record the bioelectrical signal to generate a signal recording and provide the signal recoding with connection quality data points in response to the determined impedance.

The processor may be configured to direct the plurality of electrodes to provide an electrical stimulation signal with one or more electrodes of the plurality of electrodes. The electrical stimulation signal may be configured to provide stimulation of one or more of a nerve, a spinal cord nerve, a peripheral nerve, a skeletal muscle, a smooth muscle, or cardiac tissue.

The processor may be configured to direct the plurality of electrodes to provide the electrical stimulation signal after a plurality of impedances for the plurality of electrodes has been determined to assess connection quality between the plurality of electrodes and the tissue of the subject.

Aspects of the present disclosure also provide methods of providing an electrode connection quality assessment to a user. An impedance measurement of an electrode coupled to a subject may be scaled to be within a predetermined value range (step (a)). The scaled impedance measurement may be sorted into a selected qualitative connection quality category of a plurality of qualitative connection quality categories (step (b)). One or more of the scaled impedance measurement or the selected qualitative connection quality category for the electrode coupled to the subject may be visually displayed (step (c)).

The impedance measurement of the electrode may be nonlinearly scaled to within the predetermined value range.

The plurality of qualitative connection quality categories may comprise a good connection quality category, a marginal connection quality category, and a poor connection quality category.

The selected qualitative connection quality may be visually displayed by a color or pattern correlated to the selected qualitative connection quality.

The electrode coupled to the subject may comprise an EEG electrode, an ENG electrode, an ECG electrode, an EKG electrode, or an EMG electrode.

The steps (a) to (c) may be repeated for a plurality of electrodes coupled to the subject.

The method may further comprise steps of (d) measuring a bioelectrical signal with the electrode coupled to the subject, (e) storing the measured bioelectrical signal for subsequent analysis, and (f) tagging a region of the stored bioelectrical signal with one or more of the impedance measurement or the selected qualitative connection quality category at the time of measurement.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

Figure 1A:
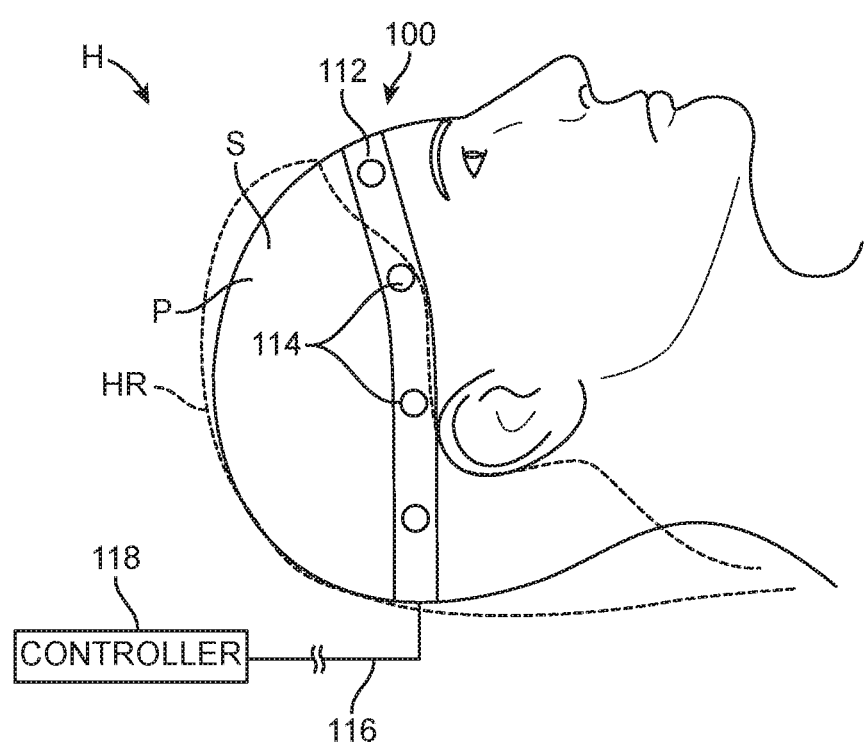
FIG. 1A illustrates a side view of a patient with an electrode carrier system configured as a headband for EEG, in accordance with some embodiments.

The present disclosure relates to systems, devices, and methods for calibrating the connection between the electrode(s) of such measurement and/or stimulation devices and the tissue of the living subject, typically skin. Aspects of the present disclosure include methods and mechanisms for assessing electrode connection quality that may be applicable for bioelectrical signal measurement such as EEG, ECG, and EMG as well for providing electrical stimulation signals to the heart, nerves, muscles, skin, and other tissue. Many embodiments herein for assessing electrode connection quality are described with reference to EEG measurement, but are applicable to other bioelectrical measurement and electro-stimulation modalities. EEG and ECG signals are typically visually displayed to a medical professional or analytical algorithm for diagnostic or scientific purposes.

In many embodiments, the measured bioelectrical signal may be sonified or converted to audio form. When represented in visual or graphical form, subtle features and attributes—and subtle changes in features and attributes—of the electrical signals may not always be easily discernible. However, when sonified or converted to auditory form, these subtle features and attributes can become more apparent to a medical professional. Furthermore, sonification methodologies that transform the signals acquired from the living subject into vocal patterns and vocal parameters—and changes in vocal patterns and vocal parameters—that resemble a human voice cam make it easier to discern, upon auditory inspection, subtleties in the underlying electrical signals that correspond to bodily function. Many embodiments herein may further include the sonification of measured bioelectrical signals, in addition to assessing electrode quality. In particular, in some embodiments, the method can transform signals acquired from the living subject into vocal patterns and vocal parameters that can be used for applications in entertainment as well as user interfaces for electronic devices. Such methods are described further in U.S. patent application Ser. No. 13/905,377 (filed 30 May 2013), Ser. No. 14/557,240 (filed 1 Dec. 2014), Ser. No. 15/159,759 (filed 19 May 2016), Ser. No. 15/387,381 (filed 21 Dec. 2016), and Ser. No. 15/783,346 (filed 13 Oct. 2017), the contents of which are incorporated herein by reference.

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

It will be understood that, although the terms "first," "second," etc. are optionally used herein to describe various elements, these elements should not be limited by these terms. These terms are only used to distinguish one element from another. For example, a first sensor could be termed a second sensor, and, similarly, a second sensor could be termed a first sensor, without changing the meaning of the description, so long as all occurrences of the "first sensor" are renamed consistently and all occurrences of the second sensor are renamed consistently. The first sensor and the second sensor are both sensors, but they are not the same sensor.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

For ease of explanation, the figures and corresponding description below are described below with reference to sonification of signals representing brain activity (e.g., electroencephalography (EEG) signals) and/or heart activity (e.g., electrocardiography (ECG) signals) of a living subject. However, one of skill in the art will recognize that signals representing other bodily functions (e.g., an electromyography (EMG) signal, or an electronystagmography (ENG) signal, a pulse oximetry signal, a capnography signal, and/or a photoplethysmography signal) may be substituted, or used in addition to (e.g., in conjunction with), one or more signals representing brain activity and/or heart activity.

Referring to FIG. 1A, an exemplary electrode carrier system 100 for measuring bioelectrical signals may generally comprise a backing 112 shown in the side view of FIG. 1A which illustrates the carrier system 100 secured around the head H of patient P. The backing 112 is shown configured as a headband in this variation although the carrier system 100 may be incorporated into any number of other platforms or positioning mechanisms for maintaining the electrodes against the patient body. The backing 112 is shown configured as a headband in this variation, and the individual electrode assemblies 114 may be spaced apart from one another so that, when the headband is positioned upon the patient's head H, the electrode assemblies 114 may be aligned optimally upon the head H for receiving EEG signals. The electrode carrier system 100 may have each of the electrodes assemblies 114 electrically coupled via corresponding conductive wires 116 extending from the backing 112 and coupled, e.g., to a controller and/or output device 118. Although in other variations, the electrodes assemblies 114 may be coupled to the controller and/or output device 118 wirelessly.

The controller and/or output device 118 may generally comprise any number of devices for receiving the electrical signals such as electrophysiological monitoring devices and may also be used in combination with any number of brain imaging devices, e.g., fMRI, PET, NIRS, etc. In one particular variation, the electrode embodiments described herein may be used in combination with devices such as those which are configured to receive electrical signals from the electrodes and process them.

The electrodes assemblies 114, as described herein, may be positioned upon the backing 112 to quickly enable conductive contact with the underlying skin while allowing for patient comfort such as when the patient P is reclined, as shown, with the back or side of their head H resting upon a surface without discomfort from the electrodes 114.

One challenge in ensuring that the individual electrodes 114 make sufficient contact with the underlying skin is the presence of hair HR on the scalp S of the patient P. In many current EEG devices, the region where the electrodes assemblies 114 are placed upon the scalp S is typically shaved to remove excess hair (if present) which interferes and inhibits electrical contact between the electrode assemblies 114 and the scalp surface. By contrast, the electrode carrier assemblies of the electrode carrier system 100 enable rapid reliable electrical contact on individual electrode assemblies through the hair HR and with scalp surface without having to remove the hair. Nevertheless, while reliable electrical contact without removing hair may be provided, systems and methods to quantify and or otherwise assess electrode connection quality may still be desired. The systems, devices, and methods to provide the aforementioned rapid and reliable electrode contact are described in U.S. patent application Ser. No. 15/387,381 (filed 21 Dec. 2016) and Ser. No. 15/783,346 (filed 13 Oct. 2017), which are incorporated herein by reference.

Figure 1B:
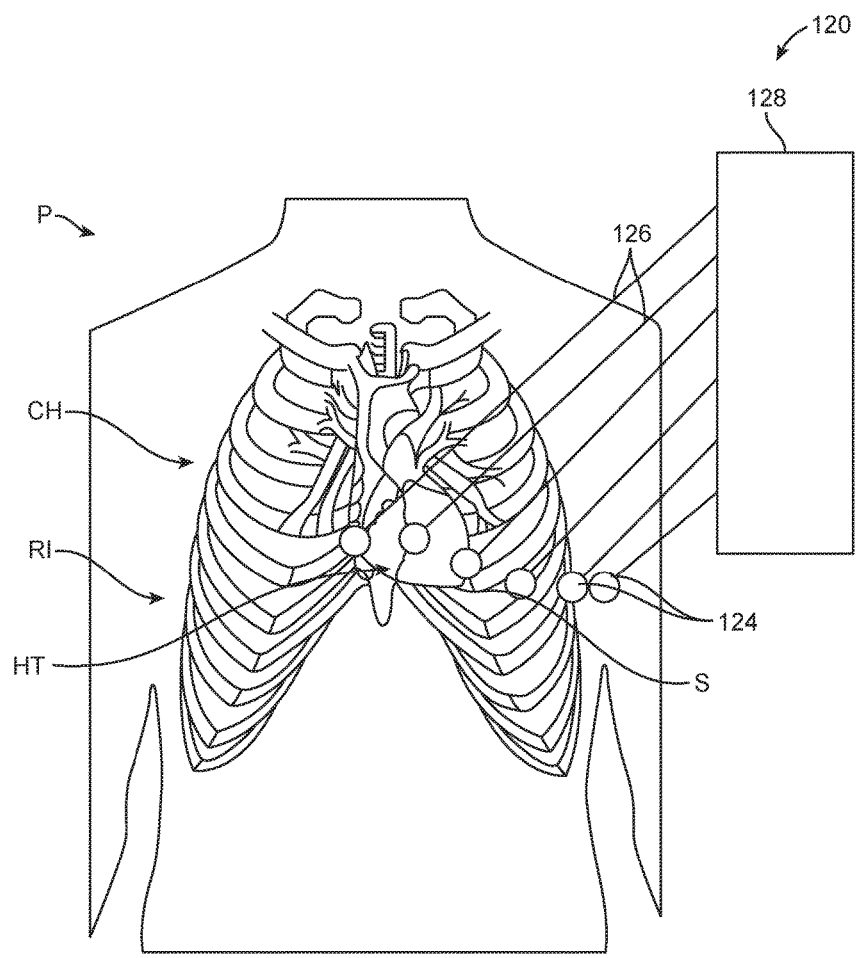
FIG. 1B illustrates a view of an electrode system for ECG on a patient chest, in accordance with some embodiments.

While an EEG system is described above, many embodiments herein for assessing electrode connection quality are also applicable to other bioelectrical measurement and electro-stimulation modalities. FIG. 1B illustrates a view of an electrode system 120 for ECG on a chest CH of the patient P, in accordance with some embodiments. The chest CH is shown with a view of the heart HT and ribs RI in order to show an exemplary placement of the electrode system 120 on the patient skin over the anatomy. The electrode system 120 may comprise a carrier system incorporated into a platform or positioning mechanism, such as a carrier system integrated into a shirt. Additionally or alternatively, each of the individual electrode assemblies 124 may be attached individually to the skin S of the patient. Each of the individual electrode assemblies 124 may be spaced by a skilled operator (e.g., a medical professional) or within the positioning mechanism such that they are aligned optimally on the patient chest to measure ECG signals. As shown in FIG. 1B, individual electrode assemblies 124 may be placed at approximately the six standard locations for the precordial leads in an ECG; however, individual electrode assemblies may be placed on the patient in any locations appropriate to receive ECG signals. Individual electrode assemblies may additionally or alternatively be placed on the limbs of the patient P, for example. The system 120 may have each of the electrode assemblies 124 electrically coupled via corresponding conductive wires 126 to a controller and/or output device 128. Although in other variations, the electrode assemblies 124 may be coupled to the controller and/or output device 128 wirelessly.

The controller and/or output device 128 may generally comprise any number of devices for receiving the electrical signals such as electrophysiological monitoring devices and may also be used in combination with any number of cardiovascular imaging devices, e.g., cardiac MM, echocardiography, coronary computed tomography angiography, etc. In some embodiments, the electrode assemblies 124 may be used in combination with devices such as those which are configured to receive and process electrical signals, such as with various filters or feature identification algorithms.

Figure 1C:
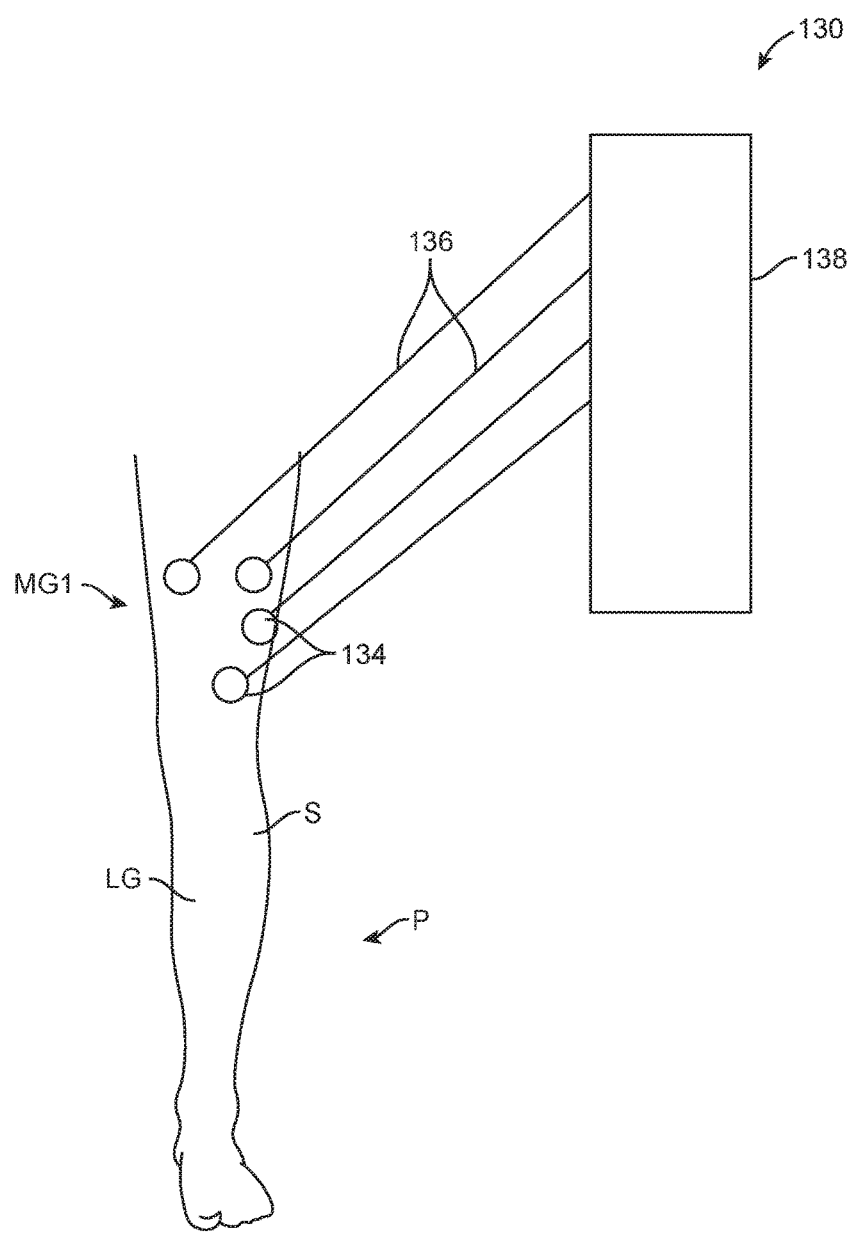
FIG. 1C illustrates a view of an electrode system for EMG on a muscle group of a patient's leg, in accordance with some embodiments.

FIG. 1C illustrates a view of an electrode system 130 for EMG on a muscle group MG1 of a leg LG of the patient P, in accordance with some embodiments. The electrode system 130 may comprise a carrier system incorporated into a platform or positioning mechanism, such as a carrier system integrated into a sock or leg band. Additionally or alternatively, each of the individual electrode assemblies 134 may be attached individually to the skin S of the leg LG. In other cases, each of the individual electrode assemblies may be placed intramuscularly, such as with monopolar needle electrode(s). Each of the individual electrode assemblies 134 may be spaced by a skilled operator (e.g., a medical professional) or within the positioning mechanism such that they are aligned optimally on the patient leg to receive the desired EMG signals. The system 130 may have each of the electrode assemblies 134 electrically coupled via corresponding conductive wires 136 to a controller and/or output device 138. Although in other variations, the electrode assemblies 134 may be coupled to the controller and/or output device 138 wirelessly.

The controller and/or output device 138 may generally comprise any number of devices for receiving the electrical signals such as electrophysiological monitoring devices and may also be used in combination with any number of musculoskeletal imaging devices, e.g., MRI, ultrasound imaging, etc. In some embodiments, the electrode assemblies 134 may be used in combination with devices such as those which are configured to receive and process electrical signals, such as with various filters or feature identification algorithms.

Figure 1D:
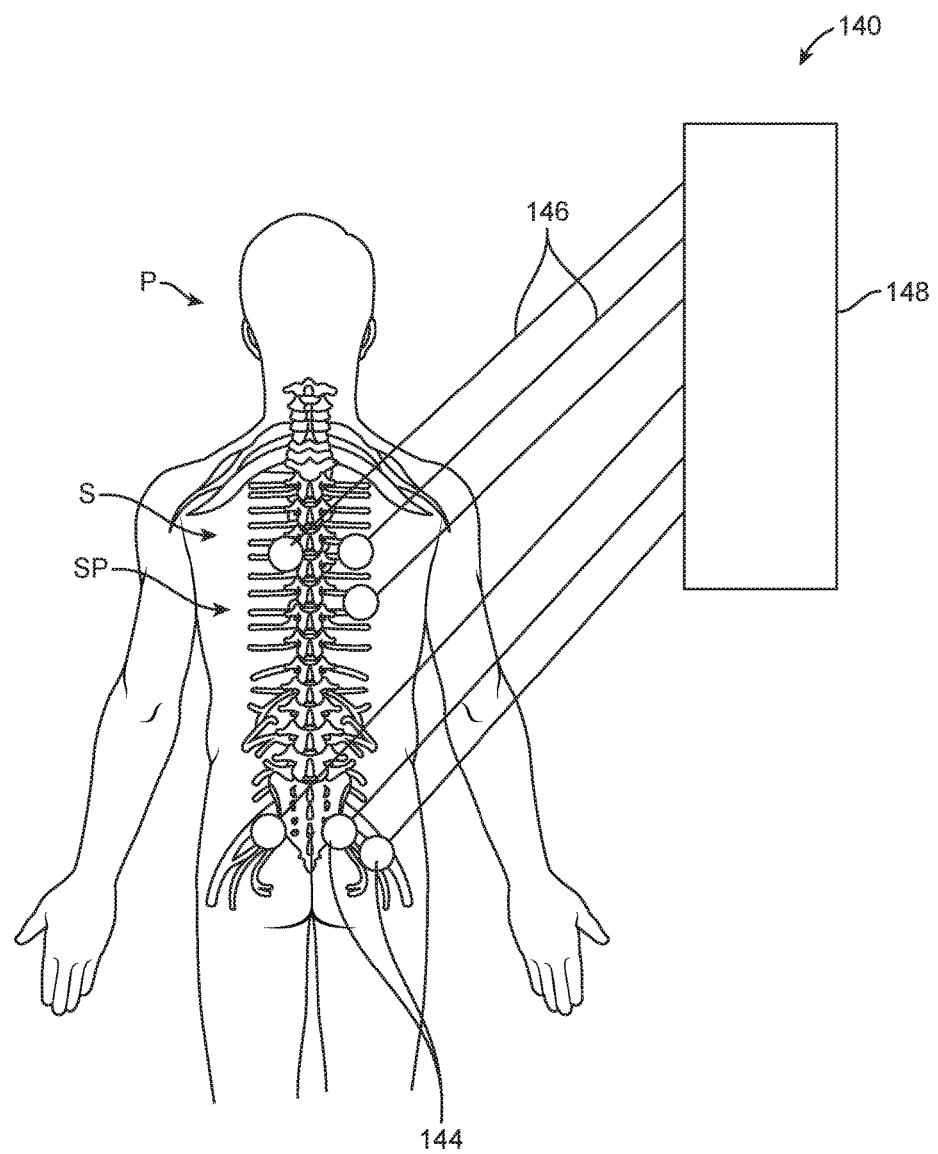
FIG. 1D illustrates a view of an electrode system for stimulation to a patient's spine, in accordance with some embodiments.

FIG. 1D illustrates a view of an electrode system 140 for stimulation on a spine SP of a patient P, in accordance with some embodiments. The back of the patient P is shown with an internal view of the patient spinal vertebrae and major nerves in order to show an exemplary placement of the electrode system 140 on the skin S of the patient P, such as used during transcutaneous electrical nerve stimulation. The electrode system 140 may comprise a carrier system incorporated into a platform or positioning mechanism, such as a carrier system integrated into a shirt. Additionally or alternatively, each of the individual electrode assemblies 144 may be attached individually to the skin S of the patient P's back. Each of the individual electrode assemblies 144 may be spaced by a skilled operator (e.g., a medical professional) or within the positioning mechanism such that they are aligned optimally on the patient P's back to output signals to stimulate the spine SP. In other cases, the individual electrode assemblies 144 are implanted subcutaneously, such as a variation on a "pain pacemaker" as known in the art. The system 140 may have each of the electrode assemblies 144 electrically coupled via corresponding conductive wires 146 to a controller and/or output device 148. Although in other variations, the electrode assemblies 144 may be coupled to the controller and/or output device 148 wirelessly.

The controller and/or output device 148 may generally comprise any number of devices for outputting the electrical signals such as electrophysiological stimulation devices and may also be used in combination with any number of cerebrospinal imaging devices, e.g., MM, spinal computed tomographic imaging, etc. In some embodiments, the electrode assemblies 144 may be used in combination with devices such as those which are configured to receive and process electrical signals, such as with various filters or feature identification algorithms.

Figure 1E:
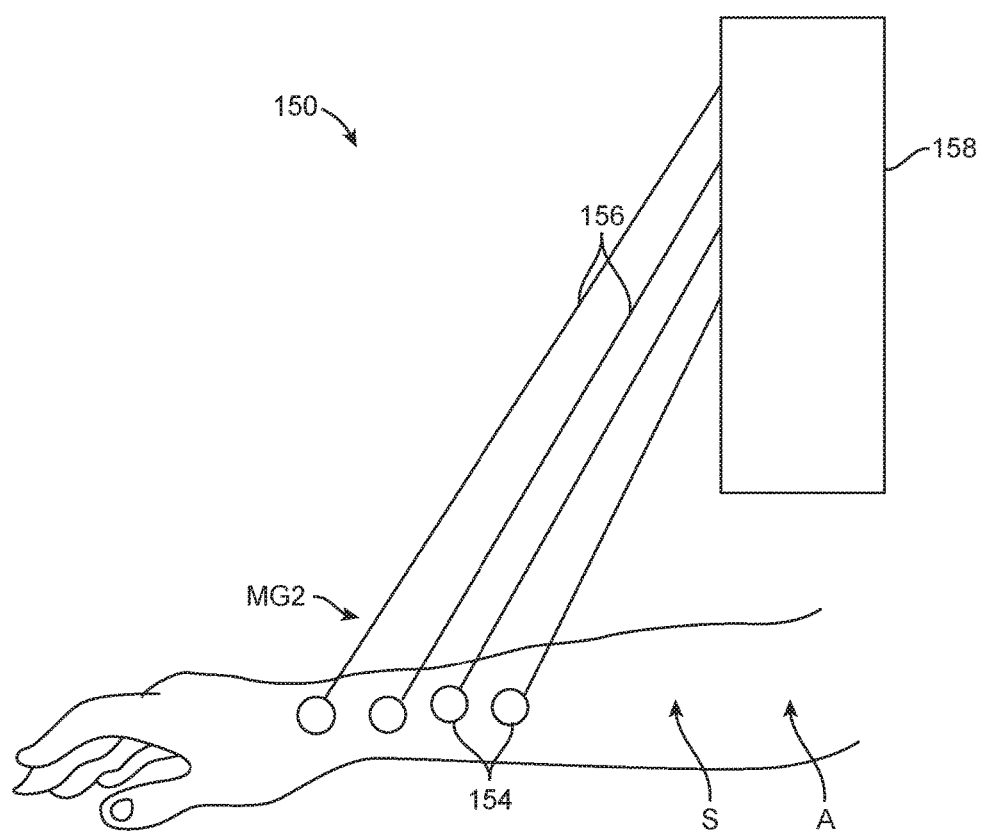
FIG. 1E illustrates a view of an electrode system for stimulation on a muscle group of a patient arm, accordance with some embodiments.

FIG. 1E illustrates a view of an electrode system 150 for stimulation on a muscle group MG2 of an arm A of the patient P, accordance with some embodiments. The electrode system 150 may comprise a carrier system incorporated into a platform or positioning mechanism, such as a carrier system integrated into a glove or a sleeve. Additionally or alternatively, each of the individual electrode assemblies 154 may be attached individually to the skin S of the arm A. Each of the individual electrode assemblies 154 may be spaced by a skilled operator (e.g., a medical professional) or within the positioning mechanism such that they are aligned optimally on the arm A to output signals to stimulate the muscle group MG2 in the arm A. The system 150 may have each of the electrode assemblies 154 electrically coupled via corresponding conductive wires 156 to a controller and/or output device 158. Although in other variations, the electrode assemblies 154 may be coupled to the controller and/or output device 158 wirelessly.

The controller and/or output device 158 may generally comprise any number of devices for outputting the electrical signals such as electrophysiological stimulation devices and may also be used in combination with any number of musculoskeletal imaging devices, e.g., MRI, ultrasound imaging, etc. In some embodiments, the electrode assemblies 154 may be used in combination with devices such as those which are configured to receive and process electrical signals, such as with various filters or feature identification algorithms.

Figure 2:
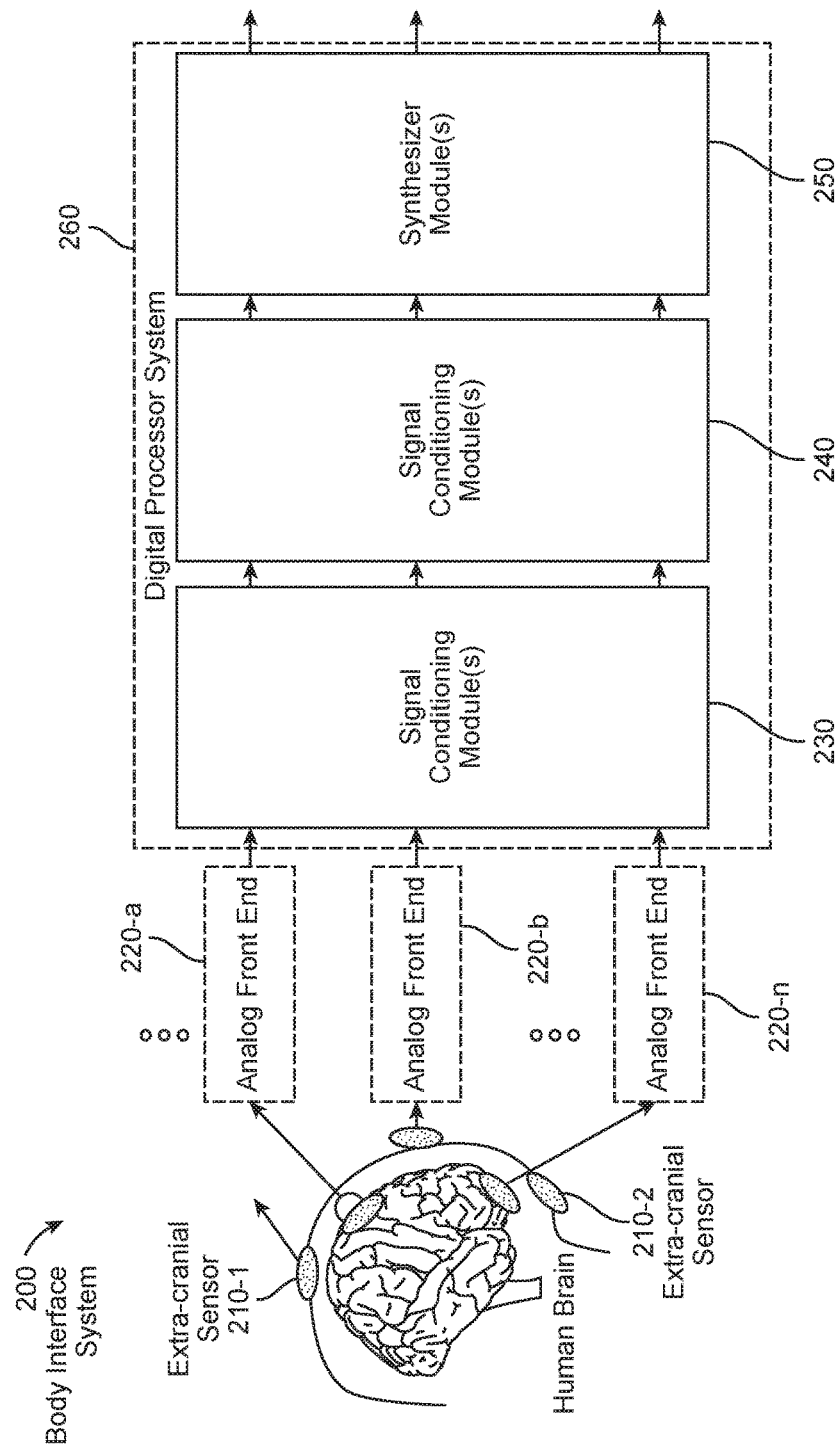
FIG. 2 is a schematic diagram illustrating a body interface system for acquiring and processing signals from a living subject, in accordance with some embodiments.
Figure 4:
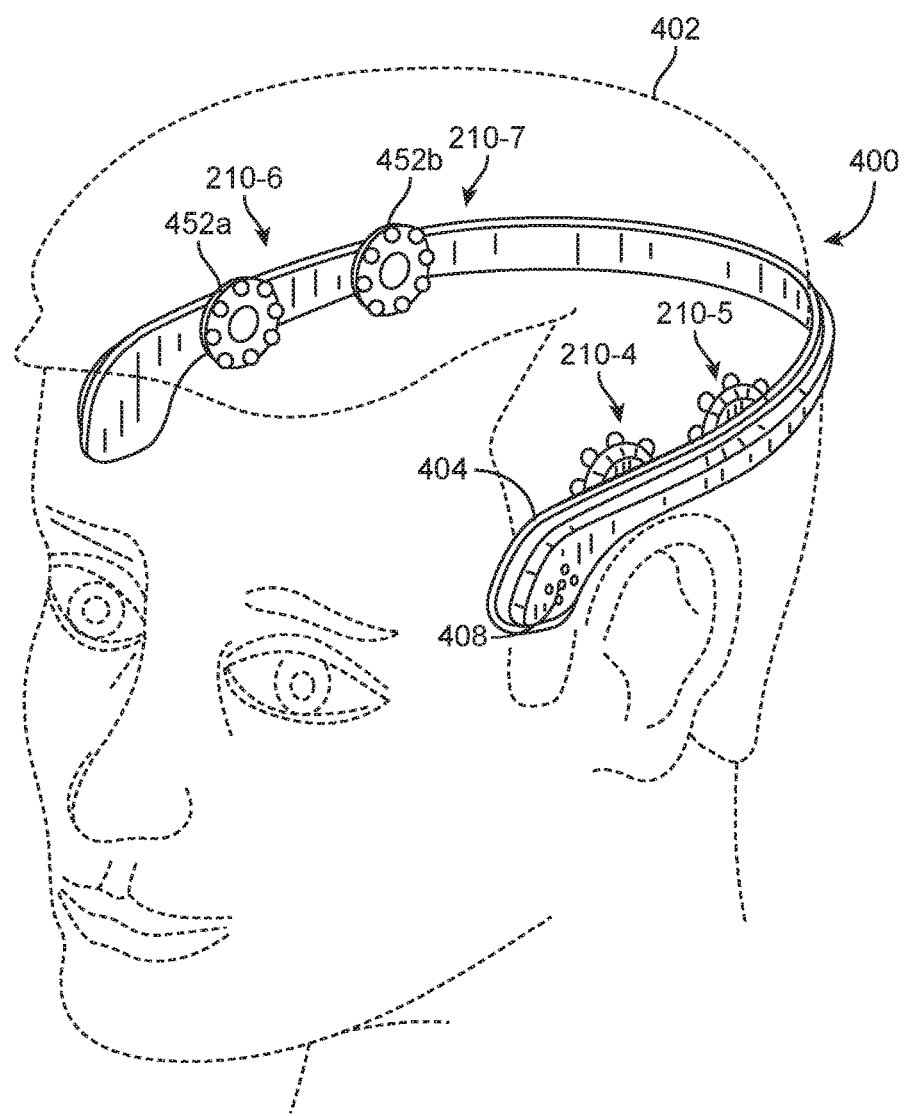
FIG. 4 is an illustration of a wearable device for sonifying electrical signals obtained from a subject, in accordance with some embodiments of the invention.

The bioelectrical measurement and/or stimulation systems described herein may include consoles, controllers, or other processing units to acquire, record, measure, process, and/or generate bioelectrical and/or stimulation signals. FIG. 2 illustrates body interface system 200 for sensing, acquiring and processing one or more signals obtained from a living subject (e.g., obtained from a human or animal's brain with the electrode carrier system 100 and similar electrode systems illustrated in FIG. 1B-1E) to produce a representation of an acoustic signal (also referred to herein as an "output acoustic signal") corresponding to the one or more signals (e.g., representing brain activity). In some circumstances, body interface system 200 is employed in a clinical setting (e.g., during or before surgical interventions and/or during diagnosis and/or treatment of conditions, such as epileptic seizures) for aural (e.g., auditory) measurement of monitoring of brain activity. Alternatively, or in addition, body interface system 200 is deployed as part of a user interface for a handheld or wearable device (e.g., a smartphone, tablet, or the like) for diagnostic, entertainment, biofeedback, monitoring, therapeutic or other purposes. In some embodiments, one or more components of body interface system 200 constitute a handheld or wearable device for sonifying electrical signals obtained from a subject, such as the head-worn electrical carrier system 100 and similar electrode systems illustrated in FIG. 1B-1E. Another example of such a wearable device for sonifying electrical signals obtained from a subject is shown in FIG. 4. In some implementations of the wearable device 400, shown in FIG. 4, digital processor system 260 is embedded in the wearable device, for example, in a "headband housing" that also holds dry or wet electrodes that contact both sides (left and right sides) of the subject's head. In some other implementations, the digital processor system 260 is not embedded in a headband housing, and is instead coupled to electrodes in (or held in position by) a headband by one or more electrical wires or connectors. Optionally, digital processor system 260 has a separate housing that includes a clip for attachment to the headband.

In some embodiments, as shown FIG. 2, the body interface system 200 includes one or more sensors 210 (e.g., sensor 210-1 and sensor 210-2), optionally includes one or more analog front ends 220 (e.g., one or more analog front end modules) and a digital processor system 260 (herein often called digital processor 260 for ease of reference) for receiving and processing signals from sensors 210. In some embodiments, digital processor system 260 includes the one or more analog front ends.

In some embodiments, sensors 210 are provided to interface with a living subject's brain to obtain e.g., sense and/or acquire) sensor time-domain signals corresponding to brain electrical activity. In some embodiments, sensors 210 are a component of a handheld device for sonifying electrical signals (such as the head-worn electrical carrier system 100 in FIG. 1, similar electrode systems illustrated in FIG. 1B-1E, and the wearable device 400 in FIG. 4). Alternatively, in some embodiments, the wearable device is configured to interface with the sensors 210 (e.g., the sensors 210 are disposable and plug into the wearable device). In some embodiments, the sensors 210 include one or more electrodes.

As an example, signals corresponding to brain electrical activity are obtained from a human brain and correspond to electrical signals obtained from a single neuron or from a plurality of neurons. In some embodiments, the one or more electrical signals represent electroencephalography (EEG) data that are concordant with laboratory EEG data. In some embodiments, sensors 210 include one or more sensors affixed (e.g., taped, attached, glued) externally to a human scalp (e.g., extra-cranial sensor 210-1). For example, extracranial sensor 210-1 may include an electrode (e.g., electroencephalography (EEG) electrode) or a plurality of electrodes (e.g., electroencephalography (EEG) electrodes) affixed externally to the scalp (e.g., glued to the skin via conductive gel), or more generally positioned at respective positions external to the scalp. Alternatively, dry electrodes can be used in some implementations (e.g., conductive sensors that are mechanically placed against a living subject's body rather than planted within the living subject's body or held in place with a conductive gel). An example of a dry-electrode is a headband with one or more metallic sensors (e.g., electrodes) that is worn by the living subject during use (FIG. 4). The signals obtained from an extracranial sensor 210-1 are sometimes herein called EEG signals or time-domain EEG signals.

In some embodiments, although not shown in FIG. 2, sensors 210 are heartbeat pulse sensors. In some embodiments, sensors 510 can be used both as EEG sensors (e.g., by placing sensors 210 on the subject's head) and as heartbeat pulse sensors (e.g., by placing sensors 210 on the subject's chest or another location where a heart signal is detectable). The heartbeat pulse sensors are provided to interface with a living subject's heart to obtain (e.g., sense and/or acquire) sensor time-domain signals corresponding to heart electrical activity. For example, signals corresponding to heart electrical activity may be obtained from a human heart and correspond to electrical signals obtained from a single cardiomyocyte or from a plurality of cardiomyocytes (e.g., a sinoatrial (SA) node of a human subject). In some embodiments, the heartbeat pulse sensors include one or more sensing elements affixed (e.g., taped, attached, glued) externally to a human body (e.g., a human subject's chest, abdomen, arm, or leg). For example, the heartbeat pulse sensors may include an electrode (e.g., electrocardiography (ECG) electrode) or a plurality of electrodes (e.g., electrocardiography ECG) electrodes) affixed externally to the human body (e.g., glued to the skin via conductive gel), or more generally positioned at respective positions external to the human body. Alternatively, dry electrodes can be used in some implementation (e.g., conductive sensors that are mechanically placed against a human body rather than being implanted within the human body or held in place with a conductive gel). An example of a dry-electrode is a chest strap with one or more metallic sensors (e.g., electrodes) that is worn by the living subject during use. Another example of a dry-electrode is a thumb apparatus or a hand apparatus with one or more metallic sensing elements (e.g., electrodes) that is touched (e.g., with the living subject's thumbs) and/or held onto (e.g., with the living subject's hands) by the living subject during use. The signals obtained from heartbeat pulse sensors are sometimes herein called ECG signals or time-domain ECG signals.

In some embodiments, heartbeat pulse sensors sense voltages corresponding to heart electrical activity. In alternative embodiments, heartbeat pulse sensors sense electrical currents corresponding to heart electrical activity. In some implementations, heartbeat pulse sensors sense differential voltages (e.g., differences in voltage values) between two measurement locations (e.g., between two sensing elements). For example, when a respective heartbeat pulse sensor includes two or more sensing elements (e.g., electrodes) positioned at respective positions external to the human body, the respective heartbeat pulse sensor may sense differential voltages (e.g., bipolar voltages) between the two or more sensing elements located at the respective positions. In some implementations, a "twelve-lead electrocardiogram" is constructed by referencing each sensing element of a set of sensing elements to one or more other sensing elements to produce a corresponding set of differential voltage signals (e.g., a twelve-lead set of differential voltage signals), each of which is a respective sensor time-domain signal.

In some embodiments, although not shown in FIG. 2, sensors 210 are sensors of electrical potential produced by skeletal muscles. In some embodiments, sensors 210 can be used both as EEG sensors and as EMG sensors (e.g. by placing sensors 210 on the patient's skin near a skeletal muscle group). The electrical potential sensors are provided to interface with a living subject's muscles to obtain (e.g. sense and/or acquire) sensor time-domain signals corresponding to muscle electrical activity. For example, signals corresponding to muscle electrical activity may be obtained from a human quadriceps and correspond to electrical signals obtained from contraction of said quadriceps. In some embodiments, the electrical potential sensors may include an electrode or a plurality of electrodes affixed externally to the human body (e.g. glue to the skin via conductive gel), or more generally positioned at respective positions external to the human body. Alternatively, dry electrodes can be used in some implementations (e.g., conductive sensors that are mechanically placed against a human body rather than being implanted within the human body or held in place with a conductive gel). Alternatively, electrodes may be implanted in the patient (e.g. into the quadriceps), such as in intramuscular EMG. The signals obtained from the electrical potential sensors are sometimes herein called EMG signals or time-domain EMG signals.

In some embodiments, EMG sensors sense voltages corresponding to muscular electrical activity. In alternative embodiments, EMG sensors sense electrical currents corresponding to muscular electrical activity. In some implementations, EMG sensors sense differential voltages (e.g., differences in voltage values) between two measurement locations (e.g., between two sensing elements). For example, when a respective EMG sensor includes two or more sensing elements (e.g., electrodes) positioned at respective positions external to the human body, the respective EMG sensor may sense differential voltages (e.g., bipolar voltages) between the two or more sensing elements located at the respective positions.

In some embodiments, arrays of sensors (e.g., sensors 210) are designed to record intracranial EEG and produce a plurality of sensor time-domain signals. In some embodiments, sensor time-domain signals include wideband features including high-gamma bursts in the range of 80-150 Hz. In some embodiments, sensor time-domain signals include frequencies (sometimes called frequency components) below (e.g., lower than or in the lowest ranges of) the human audible frequency-range.

In some implementations, analog front end 220 receives sensor time-domain signals from sensors 210 and optionally pre-processes the sensor time-domain signals to produce filtered sensor time-domain signals. In some embodiments, a separate (e.g., independent) analog front end is provided for interfacing with each of a set of sensors 210. In some embodiments, a first analog front end is provided for interfacing with a set of EEG sensors 210. A second (i.e., distinct) electrocardiography (ECG) analog front end is provided for interfacing with a set of heartbeat pulse sensors 210. A third (i.e., distinct) electromyography (EMG) analog front end is provide for interfacing with a set of sensors for the electric potential produced by skeletal muscles. In such embodiments, body interface system 200 comprises a plurality of analog front end modules (e.g., analog front end 220-*a*, analog front end 220-*b*, though analog front end 220-*n*) for interfacing with a plurality of sensors 210.

In some embodiments, although not shown in FIG. 2, sensors 210 output electrical signals to stimulate a patient nerve. In some embodiments, sensors 210 can be used both as EEG sensors and electrical nerve stimulators (e.g. by placing sensors 210 on a subject spine or another location where a patient nerve can be stimulated). The electrical nerve stimulators are provided to interface with a living subject's nerves (e.g., spinal cord) to output time-domain signals corresponding to electrical signals to stimulate a patient's nerves. For example, electrical signals may mask patient pain in order to treat chronic regional pain. In some embodiments, the nerve stimulators include one or more stimulating elements affixed (e.g., taped, attached, glued) externally to a human body (e.g., a human subject's chest, abdomen, arm, or leg). For example, the nerve stimulators may include an electrode or a plurality of electrodes affixed externally to the human body (e.g., glued to the skin via conductive gel), or more generally positioned at respective positions external to the human body. Alternatively, dry electrodes can be used in some implementation (e.g., conductive sensors that are mechanically placed against a human body rather than being implanted within the human body or held in place with a conductive gel). In other embodiments, the nerve stimulators include one or more stimulating elements implanted subcutaneously (e.g., in proximity to a patient spinal cord), such as in a Dorsal Column Stimulator.

In some embodiments, nerve stimulators output voltages to effect nerve electrical activity. In alternative embodiments, nerve stimulators output electrical currents to effect nerve electrical activity. In some implementations, nerve stimulators output multiple voltages on different electrodes in order to produce differential voltages (e.g., differences in voltage values) between two stimulation locations (e.g., between two stimulation elements). For example, when a respective nerve stimulator includes two or more stimulating elements (e.g., electrodes) positioned at respective positions external to the human body, the respective nerve stimulator may apply differential voltages (e.g., bipolar voltages) between the two or more stimulating elements located at the respective positions. The signals output from the nerve stimulators are sometimes herein called nerve stimulation signals or time-domain nerve stimulation signals.

In some embodiments, although not shown in FIG. 2, sensors 210 output electrical signals to stimulate a patient skeletal muscle. In some embodiments, sensors 210 can be use both as EMG sensors and electrical muscle stimulators (e.g. by placing sensors 210 on a subject leg or another location where a patient muscle can be stimulated). The electrical muscle stimulators are provided to interface with a living subject's musculature (e.g., a quadriceps) to output time-domain signals corresponding to electrical signals to stimulate a patient's muscles. For example, electrical signals may induce muscular contraction, for example, to prevent atrophy, to re-educate a muscle, to increase range of motion, etc. or to relax patient muscle spasms. In some embodiments, the muscle stimulators include one or more stimulating elements affixed (e.g., taped, attached, glued) externally to a human body (e.g., a human subject's chest, abdomen, arm, or leg). For example, the muscle stimulators may include an electrode or a plurality of electrodes affixed externally to the human body (e.g., glued to the skin via conductive gel), or more generally positioned at respective positions external to the human body. Alternatively, dry electrodes can be used in some implementations (e.g., conductive sensors that are mechanically placed against a human body rather than being implanted within the human body or held in place with a conductive gel). In other embodiments, the muscle stimulators include one or more stimulating elements implanted subcutaneously (e.g., in proximity to a patient quadriceps.

In some embodiments, muscle stimulators output voltages to effect muscular electrical activity. In alternative embodiments, muscle stimulators output electrical currents to effect muscular electrical activity. In some implementations, muscle stimulators output multiple voltages on different electrodes in order to produce differential voltages (e.g., differences in voltage values) between two stimulation locations (e.g., between two stimulation elements). For example, when a respective muscle stimulator includes two or more stimulating elements (e.g., electrodes) positioned at respective positions external to the human body, the respective nerve stimulator may apply differential voltages (e.g., bipolar voltages) between the two or more stimulating elements located at the respective positions. The signals output from the muscle stimulators are sometimes herein called muscle stimulation signals or time-domain muscle stimulation signals.

In some implementations, analog front end 220 outputs time-domain signals from sensors or stimulators 210 and optionally pre-processes the time-domain signals. In some embodiments, a separate (e.g., independent) analog front end is provided for interfacing with each of a set of sensors or stimulators 210. In some embodiments, a fourth analog front end is provided for interfacing with a set of nerve stimulators 210. In some embodiments, a fifth analog front end is provided for interfacing with a set of muscle stimulators 210. In such embodiments, body interface system 200 comprises a plurality of analog front end modules (e.g., analog front end 220-a, analog front end 220-b, though analog front end 220-n) for interfacing with a plurality of sensors or stimulators 210.

As shown in FIG. 2, body interface system 200 may include digital processor system 260 for processor signals obtained from the living subject (e.g., signals corresponding to electric activity and/or stimulation of the brain or heart or musculature), optionally after the signals are pre-processed by analog front end 220. Digital processor 260 may include signal conditioning modules 230, signal modulators 240, and synthesizer modules 550. In some embodiments, a separate (e.g., independent) signal conditioning module, a separate (e.g., independent) signal modulator, and/or a separate (e.g., independent) synthesizer module is provided for interfacing with each sensor or stimulator 210 in a set of two or more sensors or stimulators 210 (optionally through a separate analog front end module). In such embodiments, body interface system 200 comprises a plurality of signal conditioning modules 230 and/or a plurality of synthesizer modules 250 for interfacing with a plurality of sensors or stimulators 210 and processing signals obtained from those sensors or stimulators. In some implementations, signal modulator(s) 240 receive(s) the digitized time-domain signals output by signal conditioning module(s) 230, and concurrently generate a set of acoustic parameters, including a plurality of time-varying acoustic parameters from (e.g., using) the digitized time-domain signals. One or more of the plurality of time-varying acoustic parameters is modulated in accordance with at least the signal value of the time-domain signal. In some embodiments, a synthesizer module (e.g., synthesizer module(s) 250) combines the concurrently generated set of acoustic parameters to produce a representation of a time-domain signal.

In some embodiments, a plurality of representations of acoustic signals is combined to produce a combined acoustic signal. Alternatively, a combined acoustic signal is generated by combining acoustic signals corresponding to the plurality of representations of acoustic signals produced by digital processor system 260 Signal processing and sonification for the body interface system 200 is further described in U.S. patent application Ser. No. 13/905,377 (filed 30 May 2013), Ser. No. 14/557,240 (filed 1 Dec. 2014), and Ser. No. 15/159,759 (filed 19 May 2016), the contents of which are incorporated herein by reference.

Figure 3A:
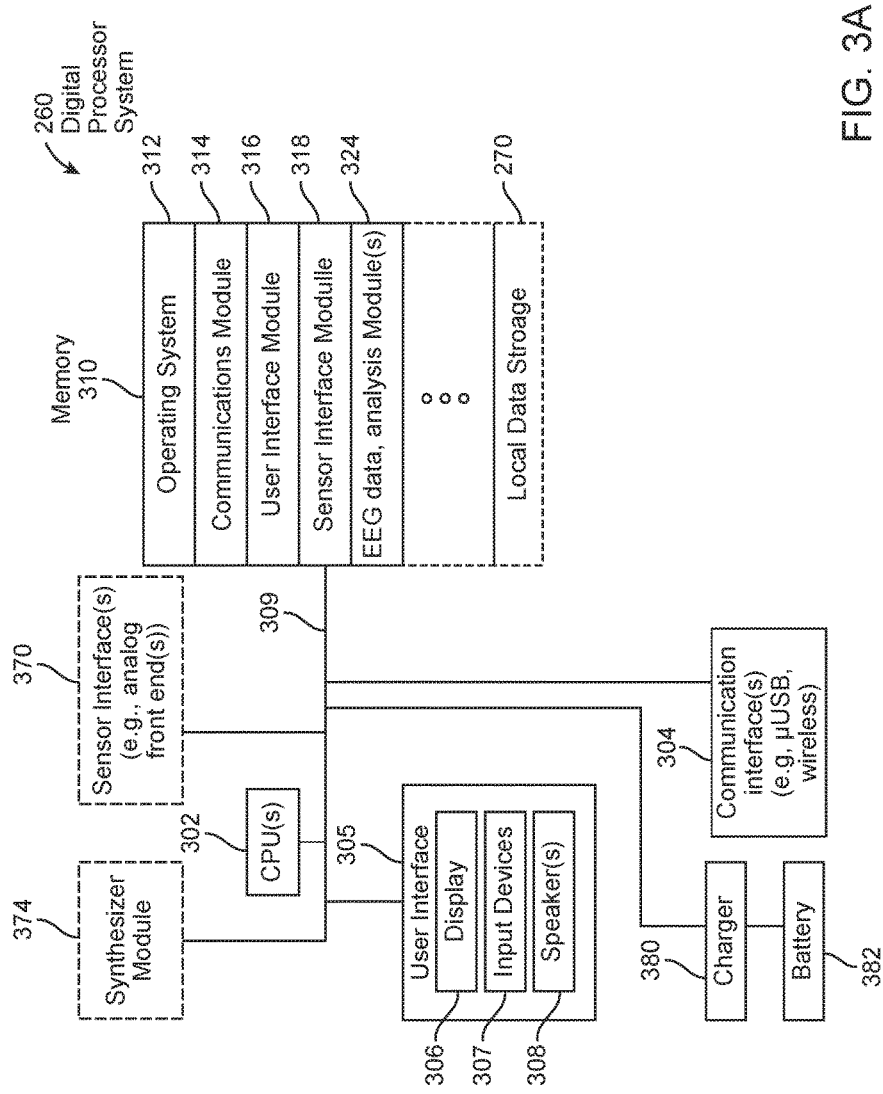
FIG. 3A is a block diagram illustrating a digital processor used for processing signals representing bodily functions, in accordance with some embodiments.
Figure 3B:
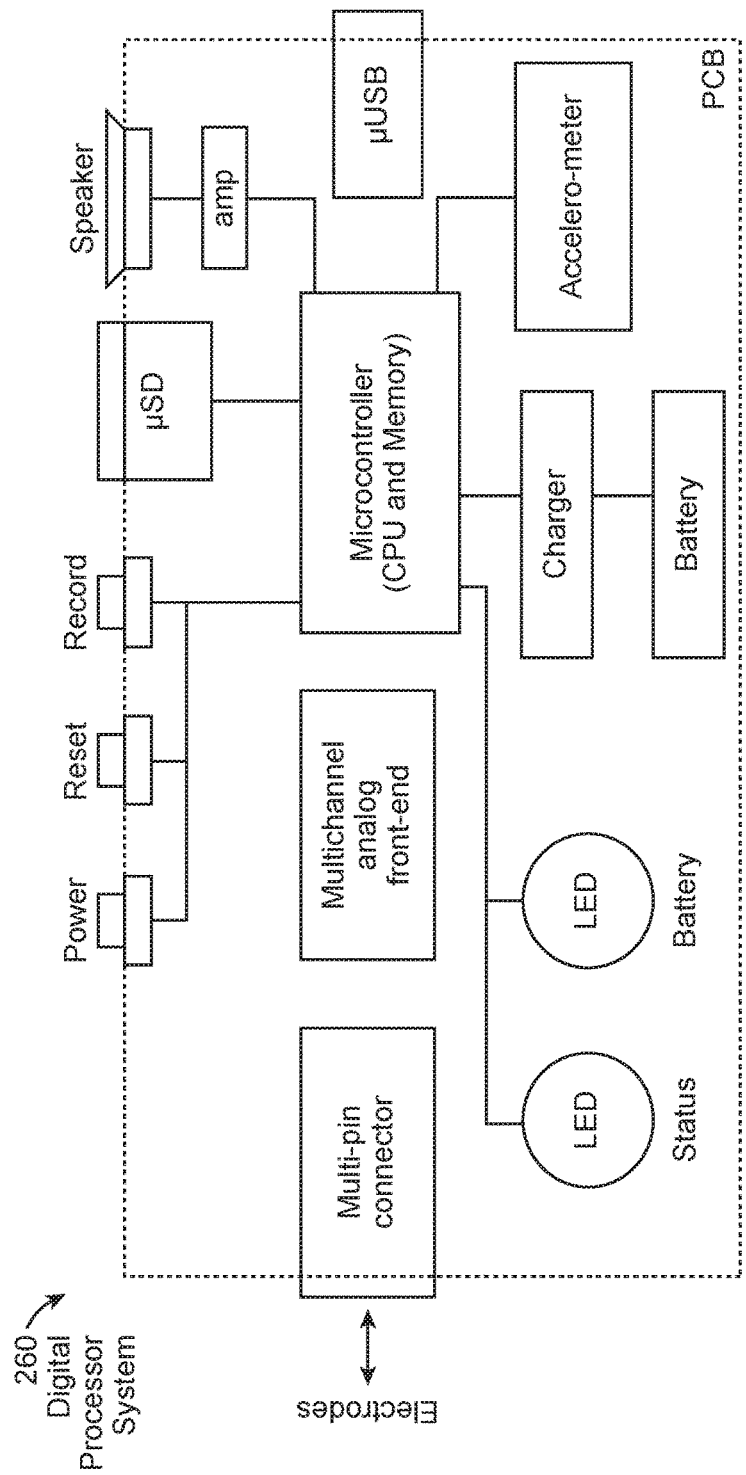
FIG. 3B is a schematic diagram of circuitry in a portable, pocket-sized handheld device for sonifying electrical signals, in accordance with some embodiments of the invention.

FIG. 3A is a block diagram illustrating digital processor system 260 in accordance with some embodiments, and FIG. 3B depicts an example of a set of components on a printed circuit board (PCB) that implement digital processor system 260. Digital processor system 260 typically includes one or more processing units (CPUs) 302 for executing modules, programs and/or instructions stored in memory 310 and thereby performing processing operations; one or more network or other communications interfaces 304 (e.g., a wired communication interface such as a USB port, micro-USB port, or the like, and/or a wireless communication interface); memory 310; and one or more communication buses 309 for interconnecting these components. The communication buses 309 optionally include circuitry (sometimes called a chipset) that interconnects and controls communications between system components. Digital processor system 260 optionally includes a user interface 305 comprising a display 306, one or more input devices 307 (e.g., one or more buttons, and, optionally, one or more of a microphone, keypad, and touch screen, etc.), and one or more speakers 308 (e.g., for audio playback of acoustic signals corresponding to brain and/or heart activity). Display 306 optionally includes one or more LEDs, for example, one or more LEDs for indicating a status of digital processor system 260 (e.g., a steady blinking LED to indicate that EEG signals are being received and/or to indicate that accelerometer signals corresponding to mechanical movement of the subject are sufficiently low-amplitude to allow DSP 260 to produce valid sonification of EEG signals) and, in another example, an LED to indicate battery status (e.g., a red LED that is turned on when battery power is low, and/or a green LED that is turned on when an internal battery is charged and that blinks on and off in a predefined pattern when battery power is low).

As shown in FIG. 3B, in some embodiments, input devices 307 may include a power on/off button for powering digital processor system 260 on and off, a reset button for resetting digital processor system 260 to a predefined initial state, and a record button for starting and stopping recording of EEG data corresponding to a subject's brain activity. Furthermore, in some embodiments, input devices 307 include a microphone for receiving and recording a user's spoken comments made just prior to, or while, DSP 260 records EEG data corresponding to a subject's pressing of the "record" button shown in FIG. 3B. Digital processor system 260 may record any spoken comments by the user for a predefined period (e.g., 5 to 10 seconds following the button press), and also records EEG data corresponding to the subject's brain activity or other digitized time domain data until the user presses the record button a second time, or until a predefined period of time elapses (e.g., 5 minutes), or until a predefined period of time (e.g., 5 minutes) elapses during which the device (digital processor system 260) does not receive electrical signals corresponding to abnormal brain activity or other abnormal electrical activity or other cue to stop collection.

Digital processor system 260 optionally includes sensor interfaces 370 for interfacing with sensors or stimulators 210 (FIG. 2) and/or analog front end 220 (FIG. 2) and synthesizer module 374 for combining concurrently generated acoustic parameters to produce a representation of an acoustic signal corresponding to one or more time-domain signals. As explained in more detail below, in some embodiments, sensors 210 are located, at least in part, within the same housing that holds digital processor system 260, while in some other embodiments, sensors or stimulators 210 are located external to that housing and are coupled to digital processor system 260 via one or more electrical connectors and sensor interface(s) 370.

Digital processor system 260 optionally (and typically) includes a battery 382 (e.g., a rechargeable battery) and charger 380, to provide power to digital processor system 260 and enable operation of digital processor system 260 without connection to an external power source (except to charge battery 382). In some embodiments, battery 382 is charged via charger 380, when an external power source is connected to system 260 via a USB port or micro-USB port of the device.

Memory 310 may include high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 310 optionally includes one or more storage devices remotely located from the CPUs 302, memory 310, or alternately the non-volatile memory devices within memory 310, comprises a non-transitory computer readable storage medium. In some embodiments, memory 310, or the computer readable storage medium of memory 310 stores the following programs, modules and data structures, or a subset thereof:

- Operating system 312 that may include procedures for handling various basic system services and for performing hardware dependent tasks;
- Network communication module 314 that may be used for connecting digital processor system 260 to other computers via the one or more communication network interfaces 309 (wired or wireless) and one or more communication networks, such as the Internet, other wide area networks, local area networks, metropolitan area networks, and so on;
- User interface module 316 that may receive commands from the user via one or more input devices 307 of user interface 315, generates user interface objects in display device 306, and optionally generates representations of signals corresponding to brain and/or heart activity, information corresponding to sensors and sensor interfaces, and information related to the configuration of body interface system 300 for display on display device 306;
- Optional local data storage 270 that may store data corresponding to the one or more electrical signals (e.g., data storage 270 stores raw EEG or other data and/or audio data so that the data can be reviewed later by, e.g., a specialist). In some implementations, data storage 270 includes a removable non-volatile memory card, such as a micro SD flash memory card (see "µSD" in FIG. 3B, which represents a micro-SD card "reader" for receiving and interfacing a micro SD flash memory card to a microcontroller). As an alternative, or in addition to data storage 270, digital processor system 260 may communicate with cloud-based storage (e.g., storage that is remote from the device) to store data corresponding to the one or more electrical signals.

Each of the above identified elements is optionally stored in one or more of the previously mentioned memory devices of digital processor system 260, and corresponds to a set of instructions for programming a function described above. The above identified modules or programs (i.e., sets of instructions) need not be implemented as separate software programs, procedures or modules, and thus various subsets of these modules is optionally combined or otherwise re-arranged in various embodiments. In some embodiments, memory 310 optionally stores a subset of the modules and data structures identified above. Furthermore, memory 310 optionally stores additional modules and data structures not described above. For example, in some embodiments, memory 310 may store one or more data analysis modules 324, for analyzing EEG or other data received by digital processor system 260 and conveying one or more results to a user of the device (e.g., via display 306 or speaker(s) 308), or to a remote device or user via communications interface 304. The one or more data analysis modules 324, if provided, may use any of a number of seizure or other pathological waveform detection methods, including data analysis methods previously developed or developed in the future.

Although FIGS. 3A-3B show digital processor system 260, FIGS. 3A-3B are intended to provide functional descriptions of the various features which are optionally present in a digital processor system, and not as a structural schematic of the embodiments described herein. In practice, and as recognized by those of ordinary skill in the art, items shown separately could be combined and some items could be separated. For example, some items shown separately in FIGS. 3A-3B could be implemented on a single digital processor system and single items could be implemented by one or more digital processor systems. The actual number of digital processor systems used to implement digital processor system 260 and how features are allocated among then may vary from one implementation to another.

FIG. 4 is an illustration of a wearable device 400 for sonifying electrical signals obtained from subject 402, in accordance with some embodiments. In other embodiments, a wearable device for sonifying electrical signals may have the form of a shirt, sock, glove etc. for sonifying signals from EMG or ECG or for sonifying signals for stimulating a patient nerve or muscle. Device 400 may include a plurality of electrodes 452 (e.g., 452a, 452b). These electrodes can be dry or wet electrodes. Electrodes 452 may be configured to be placed at respective locations on the subject's body. For example, in some embodiments, electrode 452a and electrode 452b are positioned (placed) substantially at predefined locations when subject 402 wears device 400. The plurality of electrodes may produce one or more electrical signals corresponding to brain activity. For example, device 400 may include sensors 210-4 and 210-5 which produce an electrical signal corresponding to left hemisphere brain activity, and further includes sensors 210-6 and 210-7 which produce an electrical signal corresponding to right hemisphere brain activity. Device 400 may include an analog-to-digital converter (ADC) to digitize the one or more electrical signals and a processor that receives the one or more digitized electrical signals and produces a representation of an acoustic signal. Device 400 may further include a speaker system 408 that sonifies the representation of the acoustic signal. In some embodiments, the ADC, the processor, and the speaker system are incorporated into wearable housing 404. In some embodiments, wearable housing 404 is a headband, a helmet, a hat, a sock, a glove, a shirt, pants, etc. In some embodiments, wearable housing 404 includes a headband that includes an adjustable strap or housing that is configured to fully wrap around the subject's head to stably hold the wearable housing on the subject's head. In some embodiments, device 400 interfaces with a chest strap having one or more electrodes to measure a heartbeat signal concurrently with the brain signals.

Device 400 may be used in some circumstances for long-term monitoring of rarely (e.g., sparsely or infrequently) occurring conditions. Device 400 can be worn for prolonged periods of time without becoming awkward or uncomfortable. In addition, device 400 can be easily removed for bathing and the like. This convenience can allow device 400 to monitor a patient for a month or longer, greatly increasing the likelihood that an episode will be measured by device 400 and thus produce data of an episode that is available for a medical professional to review. For example, in some embodiments, device 400 is used to produce diagnostics for neurology patients complaining of an altered mental state, such as dizziness, lightheadedness, or vertigo. As another example, in some circumstances, device 400 may be worn by epileptics and/or patients with other types of diagnosed conditions to alert them of an on-coming episode. For example, an epileptic patient may wear device 400 while driving. Device 400 may continuously monitor the epileptic patient for indicia of a pre-ictal state, which signifies that the patient is likely to start seizing. When the device detects indicia of an ictal state, the device can alert the patient using speaker 408, stating, e.g., "Pull Over! Pull Over! Seizure detected!"

Figure 5:
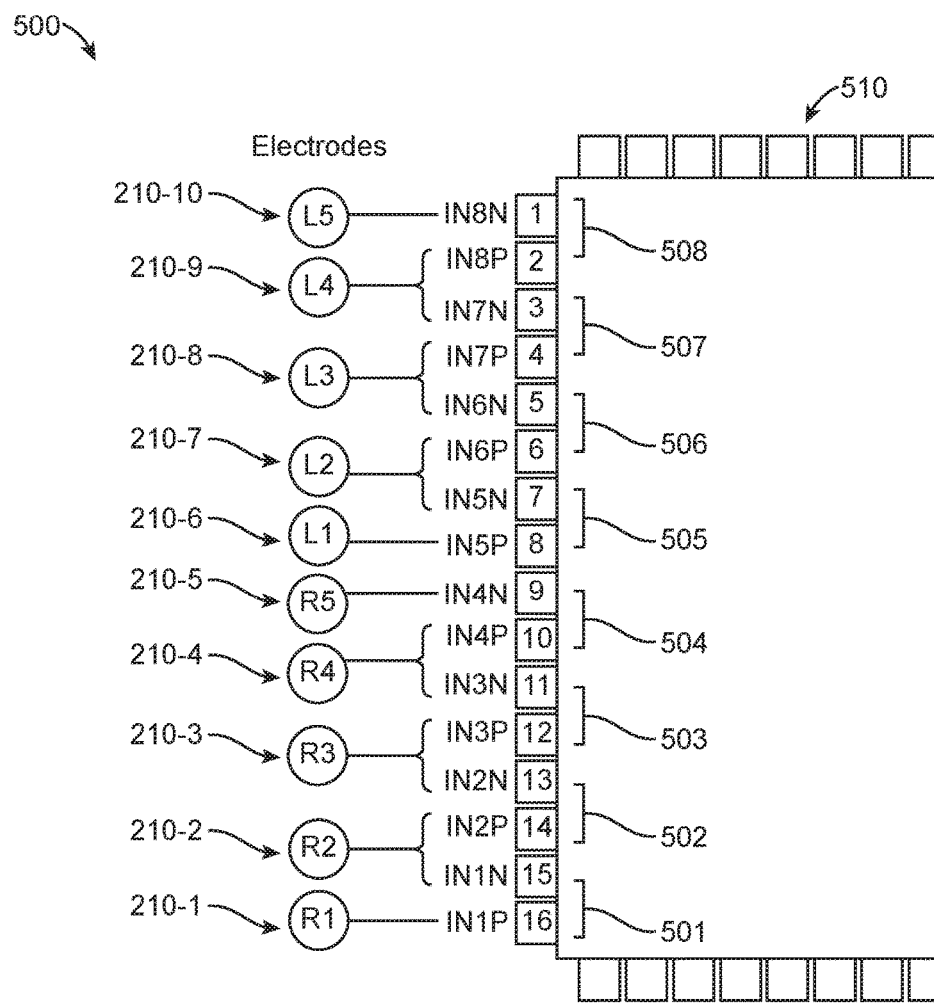
FIG. 5 is a schematic of front-end electrode connections for a signal processor that can be used to assess electrode connection quality, in accordance with some embodiments of the invention.

FIG. 5 shows a schematic 500 of front-end electrode connections for a signal processor that can be used to assess connection quality between the electrodes 210 of the wearable device 100 or 400 and the subject. The digital processor 260 of the wearable device 100 or 400 may comprise an electrode impedance check function, which can allow digital processor 260 to assess the connection quality of the EEG electrodes to the scalp of the patient and provide the assessment to the user and/or subject. The digital processor system 260 may calculate complex impedance using Ohm's Law: $V=I*Z$, where V is voltage, I is current, and Z is impedance. The impedance can therefore be calculated if the voltage is measured at a known current: $Z=V/I$. In many embodiments, a current on the order of a few nanoamps up to a few microamps (5 nA to 25 µA, for example) would work well with minimal effect on and/or sensation felt by the subject. The analog front-end chip 510 of the digital processor 260, that is, the integrated circuit (IC) containing the amplifiers and ADCs for the EEG readout, can allow a known current to be injected at a particular frequency into any of the electrodes 210.

In many embodiments, the digital processor system 260 does not have a dedicated reference electrode to measure each electrode against. Instead, each electrode 210-n can be referenced to its adjacent electrode(s). Since the ADC channels on a given hemisphere of the wearable device 100 or 400 may all be interconnected through shared electrodes 210-n (i.e., some of the electrodes 210-n may be connected to the inputs of two adjacent ADCs), the relationship between the electrodes can be used to find the voltage difference, and therefore the impedance, between any combination of two electrodes 210-n on a hemisphere.

Figure 6:
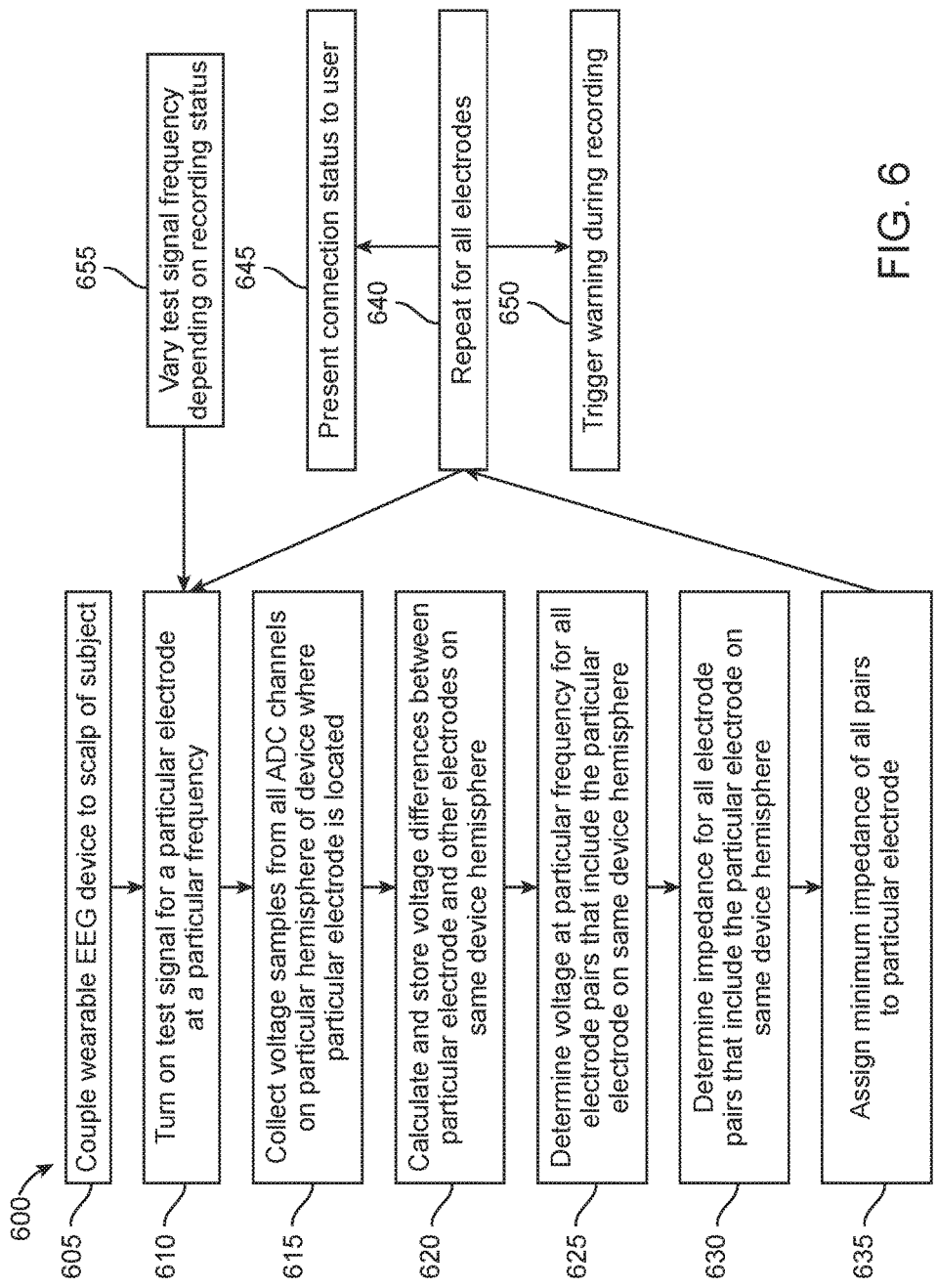
FIG. 6 is a flow chart showing a method of assessing connection quality between the electrodes of a wearable device for measuring electrical signals from the subject and/or providing electrical signals to the subject, in accordance with some embodiments of the invention.

FIG. 5 shows analog front-end electrode connections for the digital signal processor 260. There may be ten electrodes 210-1 to 210-10 connected to the 8-channel differential amplifier/ADC chip 510. The electrodes 210-1 to 210-10 can be divided into two sides covering the left and right hemispheres, with 5 electrodes on each side forming 4 differential data channels: ADC channel 501 (connected to electrodes 210-1 and 210-2), ADC channel 502 (connected to electrodes 210-2 and 210-3), ADC channel 503 (connected to electrodes 210-3 and 210-4), ADC channel 504 (connected to electrodes 210-4 and 210-5) for the left or right side, and likewise ADC channel 505 (connected to electrodes 210-6 and 210-7), ADC channel 506 (connected to electrodes 210-7 and 210-8), ADC channel 507 (connected to electrodes 210-8 and 210-9), and ADC channel 508 (connected to electrodes 210-9 and 210-10) for the opposite side, for eight data channels total. Each electrode 210-1 to 210-10 may be connected to either one or two differential amplifier inputs. The relationship between the electrodes can be used to find the voltage difference, and therefore the impedance, between any combination of two electrodes 210-n on a hemisphere as follows:

electrode 210-2–electrode 210-1=ADC channel 501, electrode 210-3–electrode 210-2=ADC channel 502, and, therefore electrode 210-3–electrode 210-1=ADC channel 502+ADC channel 501;

electrode 210-3–electrode 210-2=ADC channel 502,
electrode 210-4–electrode 210-3=ADC channel 503,
and, therefore electrode 210-4–electrode 210-2=ADC channel 503+ADC channel 502;

electrode 210-4–electrode 210-3=ADC channel 503,
electrode 210-5–electrode 210-4=ADC channel 504,
and, therefore electrode 210-5–electrode 210-3=ADC channel 504+ADC channel 503;

electrode 210-2–electrode 210-1=ADC channel 501,
electrode 210-3–electrode 210-2=ADC channel 502,
electrode 210-4–electrode 210-3=ADC channel 503,
and, therefore electrode 210-4–electrode 210-1=ADC channel 503+ADC channel 502+ADC channel 501;

electrode 210-3–electrode 210-2=ADC channel 502,
electrode 210-4–electrode 210-3=ADC channel 503,
electrode 210-5–electrode 210-4=ADC channel 504,
and, therefore electrode 210-5–electrode 210-2=ADC channel 504+ADC channel 503+ADC channel 502;

electrode 210-2–electrode 210-1=ADC channel 501,
electrode 210-3–electrode 210-2=ADC channel 502,
electrode 210-4–electrode 210-3=ADC channel 503,
electrode 210-5–electrode 210-4=ADC channel 504,
and, therefore electrode 210-5–electrode 210-1=ADC channel 504+ADC channel 503+ADC channel 502+ADC channel 501;

electrode 210-7–electrode 210-6=ADC channel 506,
electrode 210-8–electrode 210-7=ADC channel 506,
and, therefore electrode 210-8–electrode 210-6=ADC channel 506+ADC channel 505;

electrode 210-8–electrode 210-7=ADC channel 507,
electrode 210-9–electrode 210-7=ADC channel 507,
and, therefore electrode 210-9–electrode 210-7=ADC channel 507+ADC channel 506;

electrode 210-9–electrode 210-8=ADC channel 508,
electrode 210-10–electrode 210-8=ADC channel 508,
and, therefore electrode 210-10–electrode 210-8=ADC channel 508+ADC channel 507;

electrode 210-7–electrode 210-6=ADC channel 505,
electrode 210-8–electrode 210-7=ADC channel 506,
electrode 210-9–electrode 210-8=ADC channel 507,
and, therefore electrode 210-9–electrode 210-6=ADC channel 507+ADC channel 506+ADC channel 505;

electrode 210-8–electrode 210-7=ADC channel 506,
electrode 210-9–electrode 210-8=ADC channel 507,
electrode 210-10–electrode 210-9=ADC channel 508,
and, therefore electrode 210-10–electrode 210-7=ADC channel 508+ADC channel 507+ADC channel 506;

electrode 210-7–electrode 210-6=ADC channel 505,
electrode 210-8–electrode 210-7=ADC channel 506,
electrode 210-9–electrode 210-8=ADC channel 507,
electrode 210-10–electrode 210-9=ADC channel 508,
and, therefore electrode 210-10–electrode 210-6=ADC channel 508+ADC channel 507+ADC channel 506+ADC channel 505;

FIG. 6 is a flow chart showing a method 600 of assessing connection quality of the electrodes of a wearable device 100 or 400 for sonifying electrical signals that is coupled to the scalp of the subject in a step 605. While FIG. 6 shows an exemplary method of assessing connection quality associated with an EEG measurement, in other embodiments, a method 600 may be used to assess the connection quality associated with sensing or applying another type of electrical signal, such as those disclosed herein. Additionally or alternatively, at a step 605, the wearable device may be coupled to a patient body in the manners disclosed herein to sense or stimulate a patient. The number of electrodes tested may be at the discretion of the user. A minimum of two electrodes, without a common ground or reference electrode required, may be assessed for connection quality. Impedance values are assigned to the electrodes 210-n and presented to the user as an indicator for connection quality, either through a summary of the values or each of the impedance values themselves, for example. In many embodiments, an impedance of less than or equal to 5 kΩ would indicate good connection quality. In some embodiments, an impedance of less than or equal to 100 kΩ would signify acceptable connection quality. In some embodiments, the acceptable range of impedances is further divided into tiered ranges, for example, a good connection quality impedance range, a marginal connection quality impendence range, and a bad connection quality impedance range. In some embodiments, the upper range of the acceptable range of the impedance values may be used as a threshold above which connection quality is identified as poor and the user notified of such. To assign an impedance value to any particular one of the ten electrodes:

1) A test signal (e.g., a periodic current output such as a sinusoidal, square, or triangle wave, etc.) may be turned on in the particular electrode at a certain frequency (step 610);
2) Voltage samples from all ADC channels may be collected on the hemisphere (e.g., with four channels) where the particular electrode is located (step 615);
3) The voltage difference between the particular electrode and all other electrodes on that side may be calculated and the calculated value may be stored in buffers (step 620);
4) A frequency decomposition (e.g. FFT (Fast Fourier Transform), Goertzel Algorithm, etc.) may be performed on each buffer once a sufficient number of samples has been collected; the value of the resulting frequency spectrum at the bin corresponding to the test signal frequency allows the voltage at that frequency to be calculated and the voltage at the particular frequency for all electrode pairs that include the particular electrode on the same device hemisphere or side may be determined (step 625);
5) The impedance between the particular electrode and each other electrode on that side may be calculated using Ohm's Law, with the voltage being calculated for each electrode pair and the current of the test signal being known (step 630); and
6) The minimum impedance of all the calculated pairs may be assigned to the particular electrode (step 635), and this value may be closest to the true impedance of that electrode, and often the lower the impedance of the other electrodes, the more accurate this value can become.

After repeating the above process for all 10 electrodes (step 640), the measured impedance and/or a threshold-based electrode connection status can be presented to the user (step 645), or can trigger a "poor connection" warning during recording (step (650). The test signal frequency and the time between impedance measurements may be changed depending on whether a recording is in progress and/or the user has paused an active recording to check the impedance (step 655):

1. Before recording or while a recording is paused: impedance test signal may be set to a frequency that is within the normal EEG band (for example, between 1 Hz to 150 Hz, such as 31 Hz); measurements may be acquired in near real time, e.g. every ~2 seconds.

a. This mode may allow the user to get immediate connection quality feedback when setting up the device or fixing a poor connection during a (paused) recording.

b. The test signal frequency may be within the EEG band, making the raw EEG unusable during the measurement period, but may give an impedance measurement at a frequency that is relevant to EEG.

2. During recording: impedance test signal may be set to a frequency that is outside the normal EEG band (e.g., 125 Hz); measurements may be acquired less frequently, e.g. every minute.

a. This mode may allow the device to monitor electrode connection quality and may automatically alert the user to problems, without interfering with the recording.

b. The test signal frequency may be outside the EEG band which may allow it to be filtered from the raw EEG data.

Although the above steps show method 600 of assessing connection quality in accordance with many embodiments, a person of ordinary skill in the art will recognize many variations based on the present disclosure. The steps may be completed in different order. Steps may be added or deleted. Some of the steps may comprise sub-steps. Many of the steps may be repeated as often as beneficial to assessing connection quality.

One or more of the steps of the method 600 may be performed with the circuitry as described herein, for example, one or more of the processor or logic circuitry such as those of the digital processor system 260. The circuitry may be programmed to provide one or more of the steps of the method 600, and the program may comprise program instructions stored on a computer readable memory or programmed steps of the logic circuitry such as the programmable array logic or the field programmable gate array, for example.

Figure 7A:
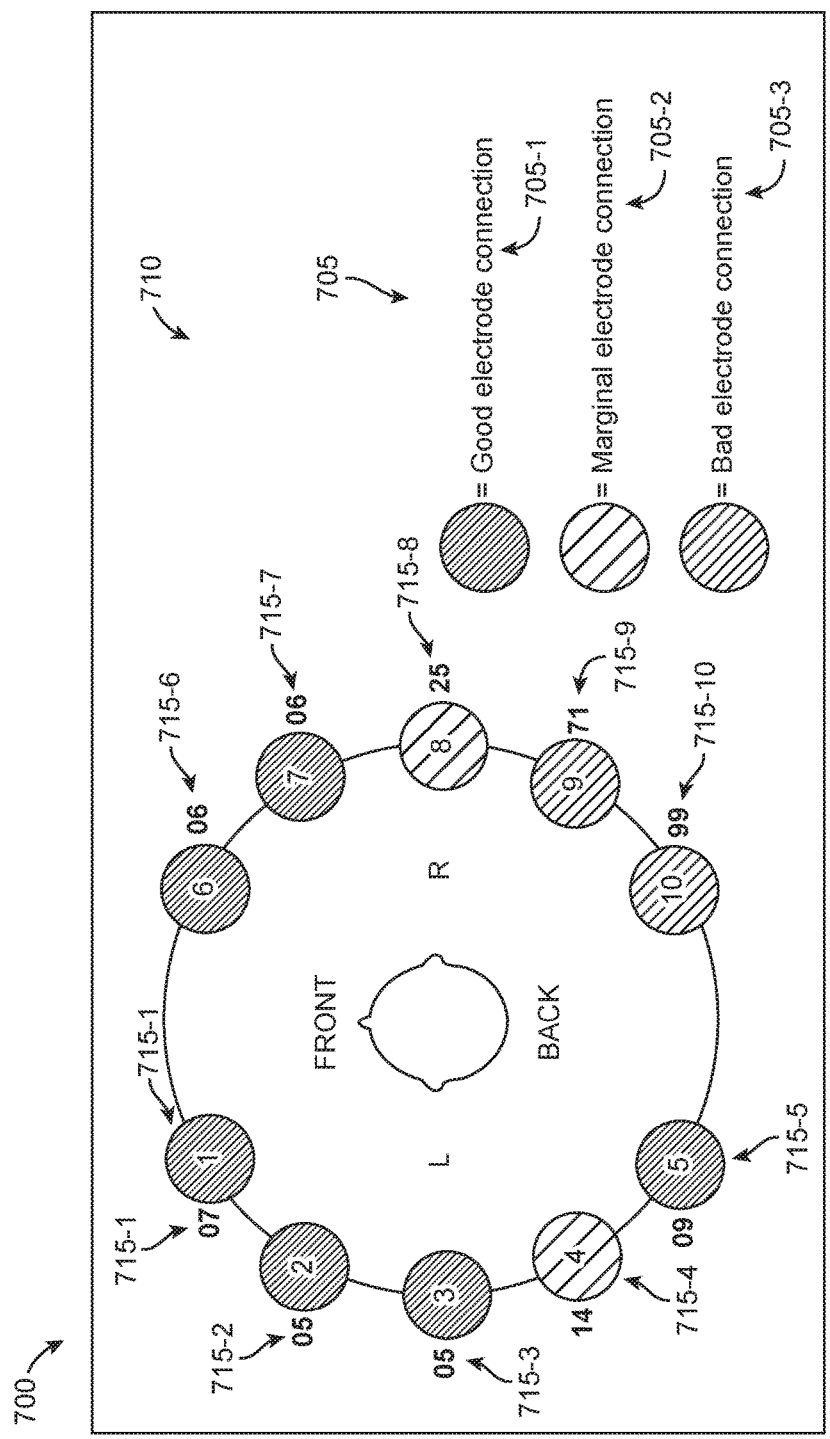
FIG. 7A shows an exemplary user interface displaying connection quality of various electrodes, in accordance with embodiments of the invention.

FIG. 7A shows an exemplary electrode check screen user interface 700 displaying connection quality of various electrodes. The user may find it difficult to intuitively understand the difference between impedance measurements themselves (e.g., 5 kΩ vs. 10 kΩ electrode impedances), and often, the dynamic range of the measurement corresponding to a poor connection (e.g., both 101 kΩ and 900 kΩ may correspond to a poor connection, and the user's action is likely the same in either case). The impedance calculated by method 600 described above may be correlated to scale which may be simpler and more useful to a user. The impedance measurements may then be presented in a more intuitive manner as shown in user interface 700 such that the user can quickly assess the state of each electrode, and whether the impedance is changing due to their efforts to improve the connection.

The impedance measurements may be mapped to a nonlinear numerical scale and presented to the user with a color-coded or otherwise patterned electrode status indicators that are visually perceptible in user interface 700. The user interface 700 may include a legend 705 to indicate which color or pattern indicates a good electrode connection 705-1, a marginal electrode connection 705-2, and a bad electrode connection 705-3. The user interface 700 includes a graphical representation 710 of electrode positions on the patient's head, including graphical representations 715-$n$ of the electrodes themselves and their respective connection quality (i.e., electrode representations 715-1, 715-2, 715-3, 715-4, 715-5, 715-6, 715-7, 715-8, 715-9, 715-10). During times when the user may be adjusting the electrodes, i.e., during setup or when recording is paused, a number indicating connection quality is displayed next to each electrode or electrode representation 715-$n$. In some embodiments, this number can range from 0 to 99, and may be scaled nonlinearly from the measured impedance. For example:

If measured impedance (kΩ) is in the range [0, 30), scaled value=$a_1 \cdot (\text{impedance})^{b1} + c_1 \rightarrow [1, 9)$ If measured impedance (kΩ) is in the range [30, 70), scaled value=$a_2 \cdot (\text{impedance})^{b2} + c_2 \rightarrow [10, 60)$ If measured impedance (kΩ) is in the range [70, 100), scaled value=$a_3 \cdot (\text{impedance})^{b3} + c_3 \rightarrow [60, 90)$ If measured impedance (kΩ) is in the range [100+], scaled value=$a_4 \cdot (\text{impedance})^{b4} + c_4 \rightarrow [90, 99)$ Where $a_n$, $b_n$, and $c_n$ are constants.

The displayed scaled value may compress the upper range of the measured impedance (poor connection) and expand the lower range (good connection), which can give the user continuous feedback in the form of a smoothly decreasing number as the connection quality improves while the skin is prepped, or the electrodes are adjusted, etc.

The graphical representation of the electrode 715-$n$ then changes colors or patterns based on the scaled impedance value, which can indicate in an immediately recognizable way whether all electrodes have acceptable connection quality, or whether some need to be adjusted. For example:

Scaled value in the range 1-10 (good electrode connection): Green electrode

For example, electrodes or electrode representations 715-1, 715-2, 715-3, 715-5, 715-6, 715-7 in user interface 700 (FIG. 7)

Scaled value in the range 11-30 (marginal electrode connection): Yellow electrode For example, electrodes or electrode representations 715-4, 715-8 in user interface 700 (FIG. 7)

Scaled value in the range 31-99 (bad electrode connection): Red electrode

For example, electrodes or electrode representations 715-9, 715-10 in user interface 700 (FIG. 7)

During an ongoing recording, the scaled numerical values may not be shown, and only the color-coded electrodes may be displayed. This can allow the user to determine at a glance whether any electrodes need to be adjusted, and whether they should pause the recording to adjust electrodes using the increased feedback granularity afforded by the scaled numerical values.

The thresholds at which the electrode graphics 715-$n$ will change colors or patterns can be user-adjustable depending on the application, and the user's needs or preferences.

Figure 7B:
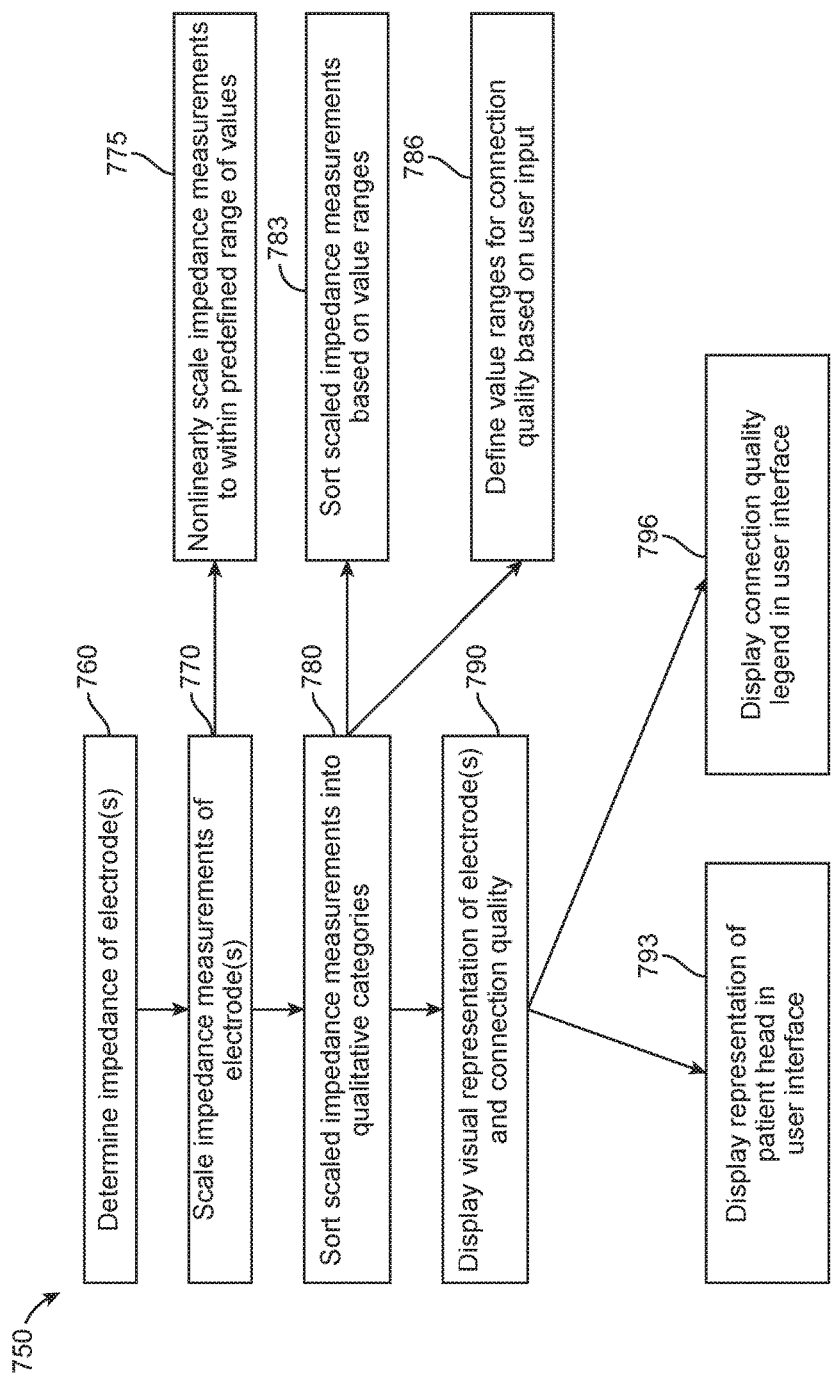
FIG. 7B is a flow chart showing a method of correlating impedance measurements with connection quality assessments for display to a user, in accordance with embodiments of the invention.

FIG. 7B is a flow chart showing a method 750 of correlating impedance measurements with connection quality assessments and displaying the connection quality assessment to the user.

In a step 760, the impedance(s) of the electrode(s) may be determined, such as in accordance with method 600 described above.

In a step 770, the impedance(s) of the electrode(s) may be scaled, such as in the manner described above. In a sub-step 775, for example, the impedance(s) may be nonlinearly scaled to within a predefined range of values such as between 0 and 99.

In a step 780, the scaled impedance measurement(s) may be sorted into qualitative categories, such as (i) good connection quality, (ii) marginal connection quality, and (iii) poor connection quality as described above. In a sub-step 783, for example the scaled impedance measurement(s) may be sorted based on their value ranges such as (i) values between 1-10 being sorted into the good connection quality category, (ii) values between 11-30 being sorted into the marginal connection quality category, and (iii) values between 31-99 being sorted into the poor quality connection category. The value ranges for each of the qualitative categories may be preset or predetermined, or they may be user defined in a sub-step 786.

In a step 790, the visual representation(s) of the electrode(s) and their connection quality may be displayed visually such as with user interface 700 shown in FIG. 7B. As described above, the user interface 700 may further include a representation of the patient's head as displayed by a step 793 and a connection quality legend as displayed by a step 796.

Although the above steps show method 750 of providing electrode connection quality assessments to a user in accordance with many embodiments, a person of ordinary skill in the art will recognize many variations based on the present disclosure. The steps may be completed in different order. Steps may be added or deleted. Some of the steps may comprise sub-steps. Many of the steps may be repeated as often as beneficial to assessing connection quality.

One or more of the steps of the method 750 may be performed with the circuitry as described herein, for example, one or more of the processor or logic circuitry such as those of the digital processor system 260. The circuitry may be programmed to provide one or more of the steps of the method 750, and the program may comprise program instructions stored on a computer readable memory or programmed steps of the logic circuitry such as the programmable array logic or the field programmable gate array, for example.

Figure 8:
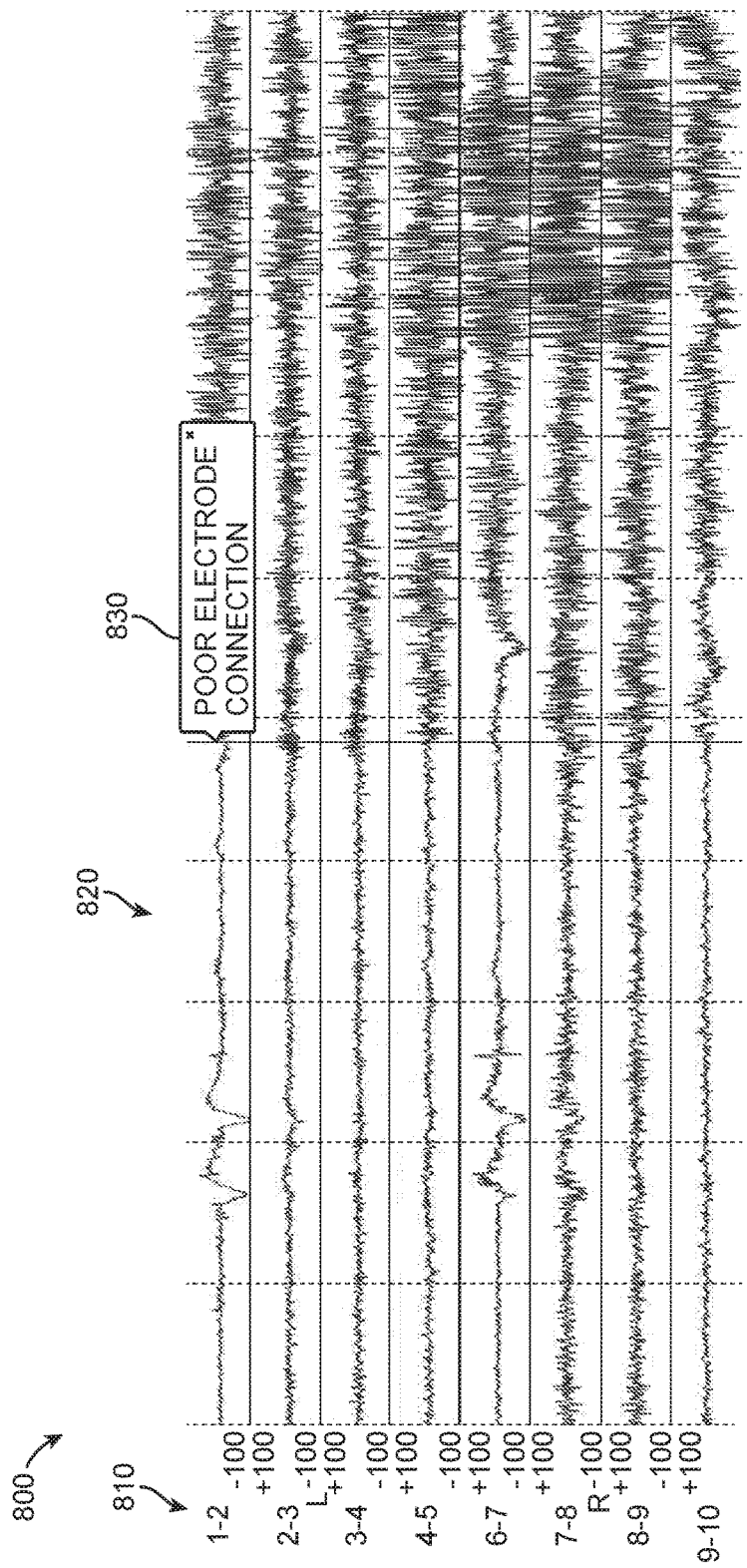
FIG. 8 shows an exemplary user interface displaying bioelectrical signal readings including one or more tags to indicate electrode connection quality at the time of the measurement of the bioelectrical signal, in accordance with embodiments of the invention.

Measurements and displays of electrode connection quality may not only assist with the user in optimizing electrode connection prior to measuring the bioelectrical signals of interest or applying electrostimulation, but may also be useful with the user in analyzing the bioelectrical signal(s) measured. For example, the user may choose to discount the bioelectrical signal(s) that are taken with electrode(s) of poor or marginal electrode connection quality and/or may choose to particularly note the bioelectrical signal(s) that are taken with electrode(s) of good connection quality. The user may do this in real-time as a displayed user interface concurrently show the bioelectrical signal(s) and connection quality assessments. Alternatively or in combination, the bioelectrical signal(s) may be recorded and stored along with their connection quality assessments for subsequent analysis. FIG. 8 shows an exemplary user interface 800 displaying bioelectrical signal readings 820 as sorted by the electrode pair 810 measuring the respective bioelectrical signal. The bioelectrical signal readings 820 may include one or more tags 830 to indicate electrode connection quality at the time of the measurement of the bioelectrical signal.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

The invention claimed is:

1. A method of assessing quality of a connection between an electrical sensor or stimulator and tissue of a subject, the method comprising:
   (a) providing an electrical sensor or stimulator comprising a plurality of electrodes;
   (b) contacting the plurality of electrodes to tissue of a subject;
   (c) providing a test signal to the tissue of the subject through a first electrode of the plurality of electrodes;
   (d) determining, with a processor coupled to the plurality of electrodes, at least one voltage difference between the first electrode and another electrode of the plurality of electrodes in response to the test signal, wherein the at least one voltage difference is determined with neither the first electrode nor the another electrode being a common ground or a common reference electrode,
   wherein determining the at least one voltage difference comprises (i) determining a first voltage difference between the first electrode and only a second electrode with the test signal provided through the first electrode and (ii) determining a second voltage difference between the first electrode and only a third electrode with the test signal provided through the first electrode, wherein the at least one voltage difference is determined with neither the first electrode, the second electrode, nor the third electrode being a common ground or a common reference electrode;
   (e) determining, with a processor coupled to the plurality of electrodes, an impedance of the first electrode in response to the determined at least one voltage difference, wherein determining the impedance comprises (i) determining a first impedance between the first electrode and only the second electrode in response to the first voltage difference, (ii) determining a second impedance between the first electrode and only the third electrode in response to the second voltage difference, (iii) determining a lesser of the first and second impedances, and (iv) assigning the lesser of the first and second impedances as the determined impedance of the first electrode; and
   (f) notifying, with an output device coupled to the processor, one or more of the subject or a user that connection quality of the first electrode is poor if the determined impedance of the first electrode is above a predetermined impedance threshold.

2. The method of claim 1, wherein the first and second electrodes are adjacent one another.

3. The method of claim 1, wherein the electrical sensor or stimulator comprises a one or more of a wearable headset, an electrode patch, or an electrode lead advanceable through the tissue, a body cavity, or a body lumen.

4. The method of claim 1, wherein the wearable sensor comprises a wearable headset.

5. The method of claim 1, wherein the plurality of electrodes comprises a first set of electrodes on one side of the electrical sensor or stimulator and a second set of electrodes on a second side of the electrical sensor or stimulator opposite the first side.

6. The method of claim 5, wherein the electrical sensor or stimulator comprises a wearable headset comprising a first hemisphere and a second hemisphere, and wherein the plurality of electrodes comprises a first set of electrodes on the first hemisphere and a second set of electrodes on the second hemisphere.

7. The method of claim 1, wherein the tissue of the subject comprises a skin of the subject, muscle tissue of the subject, or neural tissue of the subject.

8. The method of claim 7, wherein the tissue of the subject comprises a skin of the subject.

9. The method of claim 8, wherein the skin of the subject comprises a scalp of the subject.

10. The method of claim 1, wherein the test signal has a predetermined frequency, and wherein the impedance is determined in response to the predetermined frequency.

11. The method of claim 10, wherein the predetermined frequency is in a range of 1 to 150 Hz.

12. The method of claim 1, wherein the test signal is provided through the first electrode with a first predetermined current.

13. The method of claim 1, wherein the predetermined acceptable impedance threshold is in a range of 0 to 100 kΩ.

14. The method of claim 1, further comprising repeating steps (c) to (e) for at least one additional electrode of the plurality of electrodes to determine a plurality of impedances for the plurality of electrodes.

15. The method of claim 1, wherein notifying the one or more of the subject or the user comprises providing one or more of an audio or visual signal or alarm.

16. The method of claim 1, further comprising providing an electrical stimulation signal with the electrical sensor or stimulator.

17. The method of claim 16, wherein the electrical stimulation signal provides stimulation of one or more of a nerve, a spinal cord nerve, a peripheral nerve, a skeletal muscle, a smooth muscle, or cardiac tissue.

18. The method of claim 1, further comprising measuring a bioelectrical signal from the subject as the impedance of the first electrode is determined.

19. The method of claim 18, wherein the bioelectrical signal comprises one or more of an EEG signal, an ENG signal, an ECG signal, an EKG signal, or an EMG signal.

20. The method of claim 18, further comprising recording the bioelectrical signal to generate a signal recording and providing the signal recoding with connection quality data points in response to the determined impedance.

21. The method of claim 1, wherein the plurality of electrodes is coupled to a processor, and wherein the processor is configured to one or more of generate the test signal, determine the at least one voltage difference, or determine the impedance of the first electrode.

* * * * *